(12) United States Patent
Eichmann et al.

(10) Patent No.: US 7,922,738 B2
(45) Date of Patent: Apr. 12, 2011

(54) DEVICES AND METHODS FOR ACCESSING THE EPIDURAL SPACE

(75) Inventors: Stephen E. Eichmann, Cincinnati, OH (US); Zachary J. Malchano, San Francisco, CA (US); James K. Wall, San Francisco, CA (US); Kenneth S. Wu, Palo Alto, CA (US)

(73) Assignee: Insite Medical Technologies, Inc., Saratoga, CA (US)

( * ) Notice: Subject to any disclaimer, the term of this patent is extended or adjusted under 35 U.S.C. 154(b) by 220 days.

(21) Appl. No.: 11/948,980

(22) Filed: Nov. 30, 2007

(65) Prior Publication Data

US 2008/0132926 A1   Jun. 5, 2008

Related U.S. Application Data

(60) Provisional application No. 60/872,317, filed on Dec. 1, 2006.

(51) Int. Cl.
*A61B 17/32* (2006.01)
(52) U.S. Cl. ...................................................... 606/170
(58) Field of Classification Search .................. 606/159, 606/167, 170, 171, 172, 185; 604/164.01, 604/164.02, 164.05, 164.06, 164.08
See application file for complete search history.

(56) References Cited

U.S. PATENT DOCUMENTS

| | | | |
|---|---|---|---|
| 4,469,109 A | 9/1984 | Mehl | |
| 4,537,185 A | 8/1985 | Stednitz | |
| 4,670,008 A * | 6/1987 | Von Albertini | 604/165.01 |
| 4,915,697 A | 4/1990 | DuPont | |
| 4,940,458 A | 7/1990 | Cohn | |
| 4,973,305 A | 11/1990 | Goltzer | |
| 5,009,643 A | 4/1991 | Reich et al. | |
| 5,147,376 A | 9/1992 | Pianetti | |
| 5,180,382 A | 1/1993 | Frigg et al. | |
| 5,217,441 A | 6/1993 | Shichman | |
| 5,258,003 A | 11/1993 | Ciaglia et al. | |
| 5,300,035 A | 4/1994 | Clement | |
| 5,330,496 A * | 7/1994 | Alferness | 606/171 |
| 5,368,046 A | 11/1994 | Scarfone et al. | |
| 5,423,799 A * | 6/1995 | Shiu | 606/159 |
| 5,478,329 A | 12/1995 | Ternamian | |
| 5,630,805 A | 5/1997 | Ternamian | |

(Continued)

OTHER PUBLICATIONS

U.S. Appl. No. 11/250,902, filed Oct. 15, 2005.

*Primary Examiner* — Anhtuan T Nguyen
*Assistant Examiner* — David Eastwood
(74) *Attorney, Agent, or Firm* — Vista IP Law Group, LLP

(57) ABSTRACT

An apparatus for accessing the epidural space in a mammal has a cutting sheath with a distal end adapted to transition from a closed cutting configuration to an open configuration. A tissue engagement device is in a hollow portion of the sheath. The tissue engagement device has a blunt distal end and an engagement feature. A method of accessing an epidural space includes the step of forming an opening to a position at or near the ligamentum flavum using the cutting sheath. Another step of the method is positioning a tissue engagement device within the hollow portion of the cutting sheath. Another step of the method is transitioning the cutting sheath from the closed cutting configuration to the open configuration. Another step of the method is manipulating the tissue engagement device to controllably advance the tissue engagement device at least partially through the ligamentum flavum.

29 Claims, 14 Drawing Sheets

U.S. PATENT DOCUMENTS

| | | | |
|---|---|---|---|
| 5,676,682 A * | 10/1997 | Yoon | 606/185 |
| 5,685,852 A | 11/1997 | Turkel et al. | |
| 5,755,697 A | 5/1998 | Jones et al. | |
| 5,846,226 A | 12/1998 | Urmey | |
| 5,989,230 A | 11/1999 | Frassica | |
| 6,120,437 A | 9/2000 | Yoon et al. | |
| 6,379,334 B1 * | 4/2002 | Frassica | 604/165.04 |
| 6,517,519 B1 | 2/2003 | Rosen et al. | |
| 6,554,809 B2 | 4/2003 | Aves | |
| 6,565,542 B2 | 5/2003 | Kumar et al. | |
| 6,575,979 B1 | 6/2003 | Cragg | |
| 6,849,064 B2 | 2/2005 | Hamada | |
| 6,921,403 B2 | 7/2005 | Cragg et al. | |
| 7,241,297 B2 * | 7/2007 | Shaolian et al. | 606/80 |
| 7,455,666 B2 | 11/2008 | Purdy | |
| 2002/0138091 A1 * | 9/2002 | Pflueger | 606/170 |
| 2002/0177865 A1 | 11/2002 | McIntosh | |
| 2003/0130621 A1 | 7/2003 | Bryan et al. | |
| 2004/0030389 A1 | 2/2004 | Ferree | |
| 2004/0087914 A1 | 5/2004 | Bryan et al. | |
| 2006/0004457 A1 | 1/2006 | Collins et al. | |
| 2006/0036272 A1 | 2/2006 | Solsberg et al. | |
| 2006/0089633 A1 | 4/2006 | Bleich et al. | |
| 2006/0122458 A1 | 6/2006 | Bleich | |
| 2006/0184175 A1 | 8/2006 | Schomer et al. | |
| 2006/0235451 A1 | 10/2006 | Schomer et al. | |
| 2007/0149990 A1 * | 6/2007 | Palmer et al. | 606/167 |
| 2007/0198019 A1 | 8/2007 | Schomer et al. | |
| 2008/0071281 A1 | 3/2008 | Wilson et al. | |
| 2008/0103504 A1 | 5/2008 | Schmitz et al. | |
| 2008/0234717 A1 | 9/2008 | Bruszewski | |
| 2008/0275427 A1 | 11/2008 | Sage | |
| 2009/0018507 A1 | 1/2009 | Schmitz et al. | |

* cited by examiner

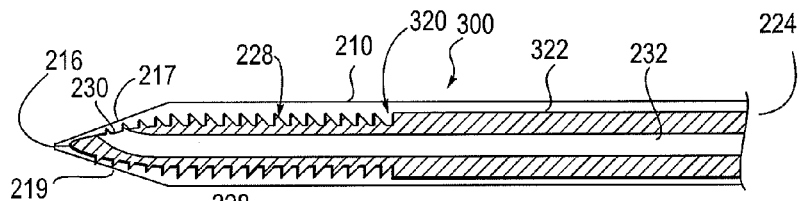
FIG. 8A
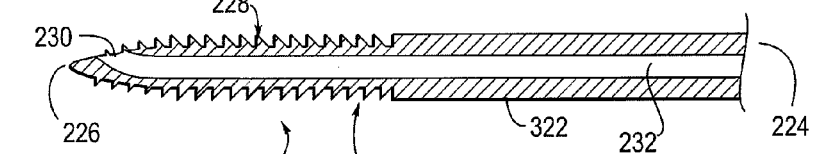
FIG. 8B
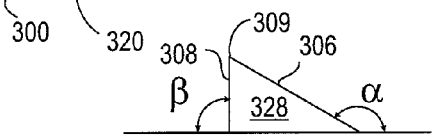
FIG. 8C
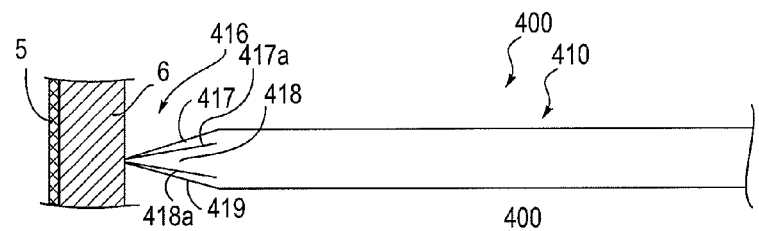
FIG. 9A
FIG. 9B
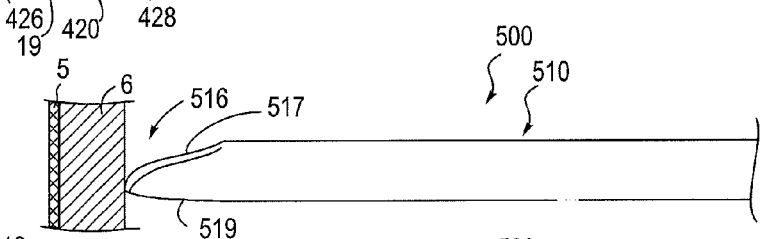
FIG. 10A
FIG. 10B

DEVICES AND METHODS FOR ACCESSING THE EPIDURAL SPACE

CROSS REFERENCE TO RELATED APPLICATIONS

This application claims priority to U.S. Provisional Patent Application Ser. No. 60/872,317 filed Dec. 1, 2006 titled "A Device to Access the Epidural Space," the entirety of which is incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

This invention relates generally to the field of anesthesia and epidural anesthesia devices to provide access to the epidural space.

BACKGROUND OF THE INVENTION

Epidural anesthesia blocks pain sensation at nerve roots that branch directly from the spinal cord by bathing them with local anesthetic agents delivered to the epidural space, a small space adjacent to the outer protective covering of the spinal cord. This route of anesthetic delivery provides an effective method for pain control during childbirth, major surgery, and chronic back pain. However, accessing the epidural space to administer anesthetic remains challenging due to its small size and proximity to the spinal cord. The currently accepted method of blindly accessing the epidural space with a straight needle is often a time consuming process of trial and error that carries a complication rate of 2-20%. The excessive time demands of placement and threat of complications result in hesitation and underutilization of epidural anesthesia. Less than half of the 7 million obstetric and surgical patients eligible for epidural anesthesia receive it.

Epidural anesthesia is a block on pain sensation at the location of the nerve roots which exit bilaterally from the spinal cord at each vertebral level. Once the needle or a small catheter is positioned appropriately, local anesthetic such as lidocaine is injected into the epidural space to bathe the spinal nerve roots, resulting in loss of pain sensation. Epidural anesthesia has been demonstrated to reduce stress response to surgery, to decrease intraoperative blood loss, to lower postoperative incidence of thromboembolic events, and to decrease morbidity and mortality in high-risk surgical patients. (See Bernards C M "Epidural and Spinal Anesthesia". *Clinical Anesthesia*, 5th Edition. Ed. Barash P G, Cullen B F, Stoelting R K. Philadelphia: Lippincott Williams & Wilkins, 2006). In addition, a catheter can be left in the epidural space for up to 5 days to provide continuous pain management in the postoperative setting, where epidural anesthesia has been demonstrated to be more effective in enabling rapid patient mobilization and earlier return of digestive function than other pathways for administering pain medications. (See Chandraskhar S and Pian-Smith M C. "Spinal, Epidural, and Caudal Anesthesia" Clinical Anesthesia Procedures of the Massachusetts General Hospital, 6th Edition. Ed: Hurford W E, Bailin M T, Davison J K, Haspel K L, Rosow C, Vassallo S A; Department of Anesthesia and Critical Care, Massachusetts General Hospital. Philadelphia: Lippincott Williams & Wilkins, 2002).

Accessing the epidural space can be extremely challenging. The epidural space is a potential space that is generally collapsed and enlarges when the tissues that bound it are separated. FIG. 1B illustrates the tissues that define the epidural space 19 including the dura mater (or dura 5) which is a protective covering that sheaths the spinal cord 4, the ligamentum flavum 6 which is a ligament adjacent to the dura 5 that runs longitudinally along the spinal column, and the bony sides of the vertebral canal. Other anatomical structures near the epidural space 19 illustrated in FIG. 1A include the pedicle 11, vertebral body 1, intervertebral disc 2, transverse process 10, spinous process 9 and a spinal nerve root 3. To access the epidural space 19, the patient is positioned either seated or on their side and instructed to flex their back outward to maximize spacing between the outer vertebral components. The spinous processes are palpated, and the interlaminar space is estimated. A needle trajectory is then chosen by the anesthesiologist and a Tuohy needle is inserted in the midline. This needle has both (1) a cutting tip which is offset in order to reduce inadvertent injury to adjacent structures and (2) a hollow lumen to allow for placement of a small catheter through which pain medication can be administered. As the needle is advanced, it passes through (in order from the skin 8): soft tissue 14, interspinous ligament 7, and ligamentum flavum 6 then ideally stops in the epidural space 19.

FIGS. 1A and 1B illustrate conventional placement of the needle 15 into the epidural space 19. FIG. 1A is a perspective view of the needle 15 in position with the surrounding anatomy. FIG. 1B is a section view the epidural space 19 showing a properly placed needle 15 and the creation of the epidural space by injecting a fluid 12 from the syringe 20 that is rigidly connected to the needle 15.

Prior to encountering the ligamentum flavum, a specially designed glass or plastic low-resistance syringe 20 filled with air or saline 12 is attached to the Tuohy needle 15. The needle 15 then is advanced slowly and gentle pressure is maintained on the syringe plunger 18 to assess the resistance to flow at the tip 16 of the needle 15. A loss of resistance to flow, as assessed through subjective feel when the air or fluid 12 is ejected from the syringe 20, indicates that the needle 15 has passed through the ligamentum flavum 6 into the epidural space 19. The needle 15 is held in position carefully to allow placement of the epidural catheter 25 then withdrawn from the epidural space over the catheter 25. Conditions such as degenerative joint disease of the spine and morbid obesity add to the difficulty of epidural access.

The challenges of accessing the epidural space can lead to complications in 2-20% of patients. The most commonly reported complications in the literature are headaches due to puncture of the dura, failure of pain blockade, backache, and epidural vein puncture. FIG. 1C illustrates a section view of the epidural space 19 with a puncture 22 in the dura 5 produced by the needle distal tip 16. FIG. 1D illustrates a section view of the epidural space 19 with an epidural vein 24 ruptured by the needle distal tip 16. FIG. 1E is a section view of the epidural space 19 with a catheter 25 improperly deployed outside the epidural space 6.

Postdural puncture headache (PDPH) is estimated to occur in 1-5% of all epidural procedures. The headache results from leakage of cerebrospinal fluid (CSF) 13 through an accidental dural puncture by the epidural needle. Initial treatment is bed rest requiring hospitalization, and in a significant number of patients with PDPH, an injection of blood into the epidural space, known as a blood patch, is required to close the inadvertent puncture site. Failure of effective pain control occurs in 5-20% of patients with 10-15% of these failures attributed to incorrect epidural catheter placement, which then results in epidural replacement or reliance on less effective means of pain control. Postoperative backache occurs in up to 30% of patients and can lead to temporary disability. Inadvertent puncture of a vein adjacent to the dura occurs in 1-11% of epidural procedures. If recognized, this is a minor complication requiring a new puncture; however, if unrecognized, catheter placement in an epidural vein can result in toxic systemic administration of anesthetic. Additional complications including significant nerve damage, meningitis, paraplegia, and death are rare (1 in 10,000 to 1 in 100,000).

The current technique of epidural access involves advancement of a Tuohy needle into the epidural space. This method relies heavily on a steady hand and the ability to immediately halt needle advancement once loss of resistance is detected to avoid damaging critical structures including the dura. Despite proven patient benefits, many practitioners are reluctant to use epidural anesthesia because of the challenges and risks described above. A survey of local practitioners revealed that excess time and fear of complications are factors that significantly limit the utilization of epidural anesthesia. What is needed are improved devices and methods for accessing the epidural space.

SUMMARY OF THE INVENTION

In one embodiment of the present invention, there is provided an apparatus for accessing the epidural space in a mammal having a cutting sheath having an open proximal end and a distal end adapted to transition from a closed cutting configuration to an open configuration. There is a hollow portion within the sheath extending from the open proximal end along the longitudinal axis of the sheath. There is a tissue engagement device disposed within the hollow portion of the cutting sheath, the tissue engagement device having an elongate body with a proximal end and a blunt distal end. There is an engagement feature on the surface of the elongate body, an aperture formed in the distal end of the elongate body; and a conduit within the elongate body in communication with the aperture and the elongate body proximal end.

In one aspect, the engagement feature on the surface of the elongate body is a screw thread. In another aspect, the screw thread comprises an asymmetric thread form or, alternatively, a reverse buttress thread form. In one alternative embodiment, the engagement feature on the surface of the elongate body comprises a plurality of ridges. In one aspect, there is also a balloon positioned within the distal end of the tissue engagement device.

In another embodiment, the cutting sheath distal end transitions from a closed cutting configuration to an open configuration by moving the elongate body within the hollow portion of the cutting sheath. In one aspect of this embodiment, moving the elongate body within the hollow portion of the cutting sheath comprises sliding the elongate body within the hollow portion of the cutting sheath. In another aspect of this embodiment, moving the elongate body within the hollow portion of the cutting sheath comprises rotating the elongate body within the hollow portion of the cutting sheath.

In one alternative embodiment, the cutting sheath includes at least one predefined movable section. In one aspect of this embodiment, the cutting sheath has a hinge that joins the at least one predefined movable section to the distal end of the cutting sheath. In another aspect, the at least one predefined movable section is defined by a scoring pattern in a sidewall of the cutting sheath. In still another aspect, the at least one predefined movable section is cut into the distal end of the sheath. In one alternative embodiment, the aperture is formed in the sidewall of the elongate body proximal to the blunt distal end. In another alternative embodiment, the aperture is formed in the blunt distal end.

Another embodiment of the present invention provides a method of accessing an epidural space in a mammal. One step of the method is forming an opening in the mammal to a position at or near the ligamentum flavum using a cutting sheath having an open proximal end and a distal end adapted to transition from a closed cutting configuration to an open configuration and a hollow portion within the sheath extending from the open proximal end. Another step of the method is positioning within the hollow portion of the cutting sheath a tissue engagement device having an elongate body with a proximal end, a blunt distal end and an engagement feature on the exterior surface of the elongate body. Another step of the method is transitioning the distal end of the cutting sheath from the closed cutting configuration to the open configuration. Another step of the method is manipulating the engagement feature on the exterior surface of the elongate body to controllably advance the blunt distal end of the elongate body at least partially through the ligamentum flavum.

In one aspect, the transitioning step includes moving the tissue engagement device relative to the cutting sheath. In one alternative aspect, moving the tissue engagement device relative to the cutting sheath comprises pulling the cutting sheath proximally relative to the tissue engagement device. In another alternative aspect, moving the tissue engagement device relative to the cutting sheath comprises rotating the tissue engagement device within the hollow central portion of the cutting sheath. In another alternative embodiment, the transitioning step includes moving a portion of the distal end of the cutting sheath about a hinge. In one aspect, at least one of the transitioning step or the manipulating step is performed by rotating the tissue engagement device. In another aspect, at least one of the transitioning step or the manipulating step is performed by longitudinal movement between the tissue engagement device and the cutting sheath. In still another aspect, there is a step of ceasing the manipulating step when a pressure drop within the tissue engagement device is detected. In yet another aspect, at least one section on the distal end of the cutting sheath moves in a predetermined manner during the opening step. In another alternative, the method also includes a step of advancing a substance, therapeutic instrument or diagnostic instrument completely through a conduit within the tissue engagement device. In another alternative, the manipulating step includes the step of inflating a balloon within the distal end of the elongate body to at least partially dissect the ligamentum flavum. In another aspect, the transitioning step exposes the blunt distal end of the tissue engagement device to the ligamentum flavum. In an alternative embodiment, the transitioning step includes removing a stylet from within the hollow portion prior to the positioning step.

In still another alternative embodiment, there is provided apparatus for accessing the epidural space in a mammal having a cutting sheath that has an open proximal end and a distal end adapted to transition from a closed cutting configuration to an open configuration. There is a hollow portion within the sheath extending from the open proximal end to the distal end. When the cutting sheath is in the closed cutting configuration, there is a stylet placed within the hollow portion. When the cutting sheath is in the open configuration, there is a tissue engagement device disposed within the hollow portion. The tissue engagement device has an elongate body with a proximal end and a blunt distal end, an engagement feature on the surface of the elongate body, an aperture formed in the distal end of the elongate body and a conduit within the elongate body in communication with the aperture and the elongate body proximal end.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 8A and 8B illustrate, respectively, a section view of an apparatus for accessing the epidural space and the tissue engagement device of FIG. 8A;

FIG. 8C is an enlarged view of an engagement feature in FIGS. 8A and 8B;

FIGS. 9A and 9B illustrate an apparatus for accessing the epidural space. FIG. 9A illustrates a perspective view of a cutting sheath having a closed cutting configuration that is completely closed shown in position against the ligamentum flavum. FIG. 9B illustrates the cutting sheath transitioned into an open configuration against the ligamentum flavum and the blunt tip and aperture of the tissue engagement device within the epidural space;

FIGS. 10A and 10B illustrate an apparatus for accessing the epidural space. FIG. 10A illustrates a perspective view of a cutting sheath having a closed cutting configuration that is completely closed shown in position against the ligamentum flavum. FIG. 10B illustrates the cutting sheath transitioned into and open configuration against the ligamentum flavum and the blunt tip and aperture of the tissue engagement device within the epidural space;

FIG. 11A illustrates a perspective view of a cutting sheath having a hinge used to transition the distal end from a closed cutting configuration to an open configuration. The sheath is closed and shown in position against the ligamentum flavum. FIG. 11B illustrates the cutting sheath where the sheath has transitioned into an open configuration against the ligamentum flavum and the blunt tip and aperture of the tissue engagement device within the epidural space;

FIG. 12A illustrates the tissue engagement device in a closed configuration. FIG. 12B illustrates the tissue engagement device in an open configuration;

DETAILED DESCRIPTION OF THE INVENTION

Embodiments of the present invention relate to devices that provide access to the epidural space and use the familiar "loss-of-resistance" technique to detect entry into the space. However, embodiments of the inventive devices have one or more advantages over existing, conventional epidural access devices and techniques. These advantages include but are not limited to (1) controlled dissection through the ligamentum flavum to safely enter the epidural space, (2) protection of the critical structures adjacent to the epidural space including the dura, spinal cord, and epidural veins, and (3) needle advancement and epidural space detection with a handpiece via a flexible cable to minimize the torque encountered with the current rigid one-piece system. These and other advantages are provided while maintaining the familiar and reliable loss-of-resistance method to detect entry into the epidural space.

Moreover, embodiments of the present invention are directed to methods and devices for providing controlled access to the epidural space. The characteristics, advantages, and techniques of controllably engaging and dissecting the ligamentum flavum during epidural space access are more fully explained in the description that follows.

Figure 2:
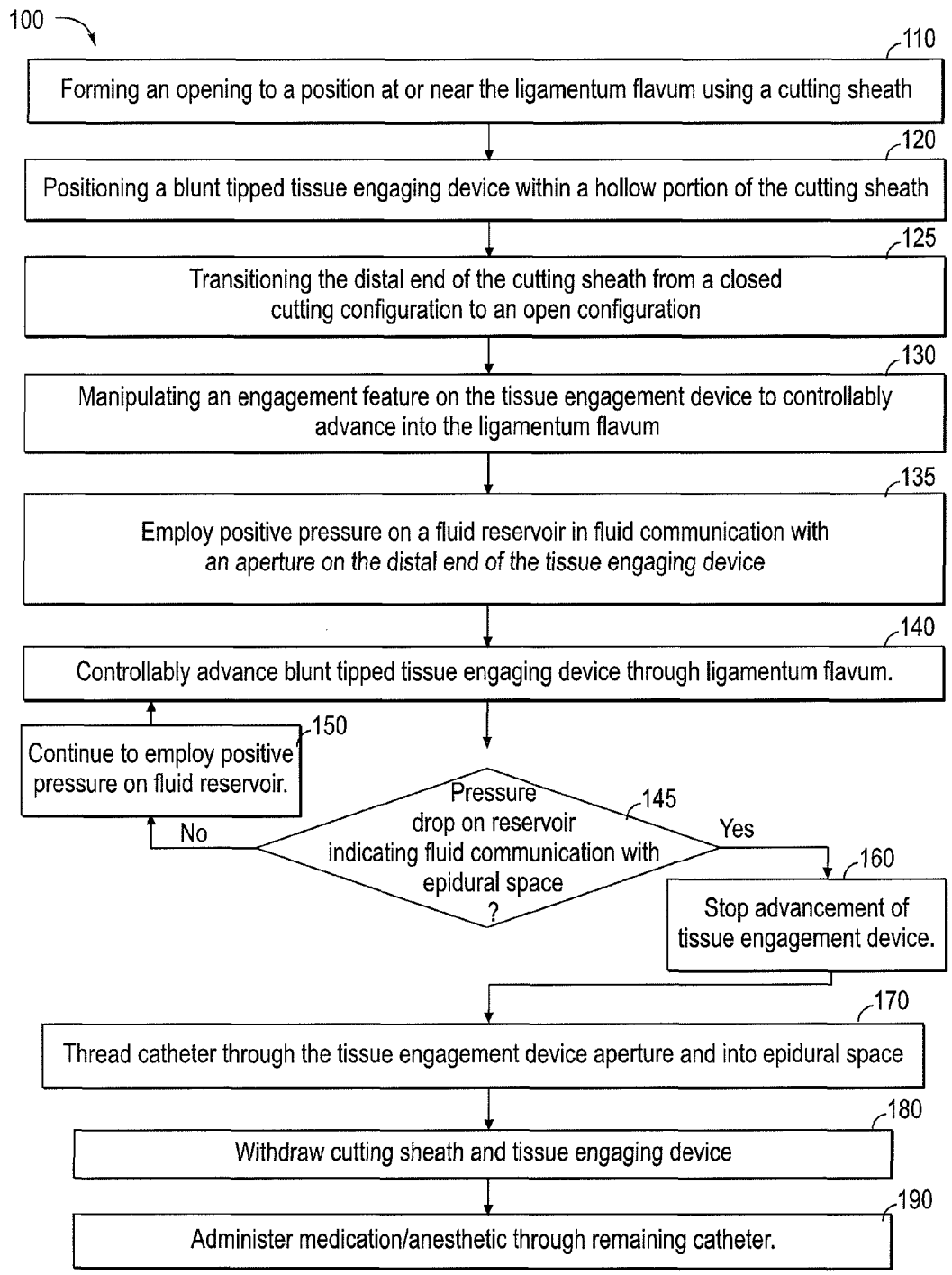
FIG. 2 is a flow chart 100 describing a method of accessing the epidural space.
Figure 3A:
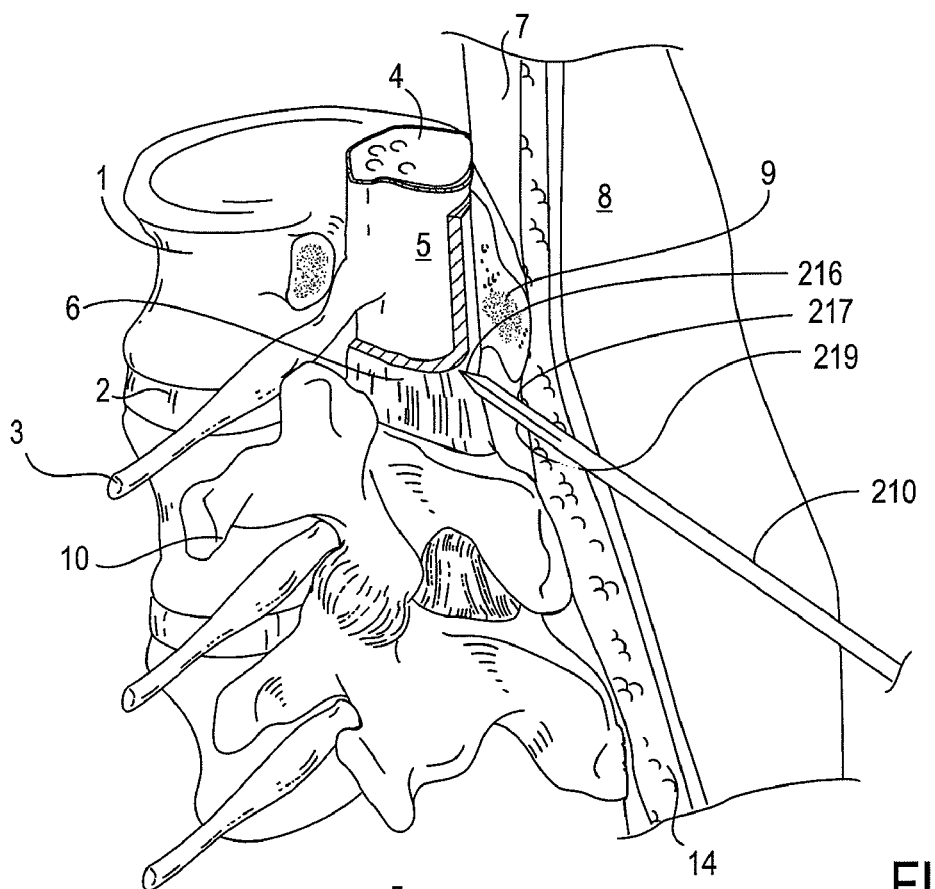
FIG. 3A is a perspective view of the ligamentum flavum and surrounding anatomical structures with a cutting sheath in a closed cutting configuration positioned at the ligamentum flavum.

One embodiment of a method for accessing the epidural space of the mammal will be described through reference to the flow chart 100 in FIG. 2. An exemplary method of epidural access will be described using an apparatus 200 for accessing the epidural space. During the discussion of an exemplary epidural access method, reference will be made to FIGS. 3A-7B that illustrate the apparatus 200 during the various steps of epidural access. The exemplary apparatus 200 includes an embodiment of a cutting sheath 210 and a tissue engagement device 220. As shown in FIGS. 3A, 3B, 4A-4H, the cutting sheath 210 has an open proximal end 212 and a distal end 216 adapted to transition from a closed cutting configuration (FIGS. 3A, 3B, 4A, 4B, 4C) to an open configuration (FIGS. 4D-4H and 5A-5B). FIGS. 4E and 4F illustrate a hollow portion 214 within the sheath 210 that extends from the open proximal end 212 along the longitudinal axis of the sheath. In the illustrated embodiments, the cutting sheath 210 terminates distally in a sharp conical apex. The shape of the cutting sheath distal end may be conical as depicted or have other shapes. An alternative shape is a rounded or bullet-shaped configuration. Embodiments of the cutting sheath of the present invention may be used to pierce, dissect, transect, and/or displace skin, soft tissue, ligaments and other structures to provide access to the ligamentum flavum.

FIGS. 4A, 4B, 4D, 4E, 4F, 4G, 4H, 5A and 5B illustrate an exemplary tissue engagement device 220 disposed within the hollow portion 214 of the cutting sheath 210. As shown in FIG. 4F, the tissue engagement device 220 has an elongate body 222 with a proximal end 224 and a blunt distal end 226. There is an engagement feature 228 on the surface of the elongate body 222. An aperture 230 is formed in the distal end of the elongate body. A conduit 232 within the elongate body 222 is in communication with the aperture 230 and the elongate body proximal end 224.

Returning to FIG. 2. First, there is the step of forming an opening to a position at or near the ligamentum flavum using a cutting sheath (step 110). FIG. 3A is a generally posterior view of a cutting sheath 210 inserted through the back, passing through skin 8 and underlying soft tissues 14 up to the ligamentum flavum 6. The sharp distal end 216 of the sheath 210 is configured to easily penetrate through skin 8 and soft tissues 14 above the ligamentum flavum 6 similar to a conventional epidural needle 15.

Figure 3B:
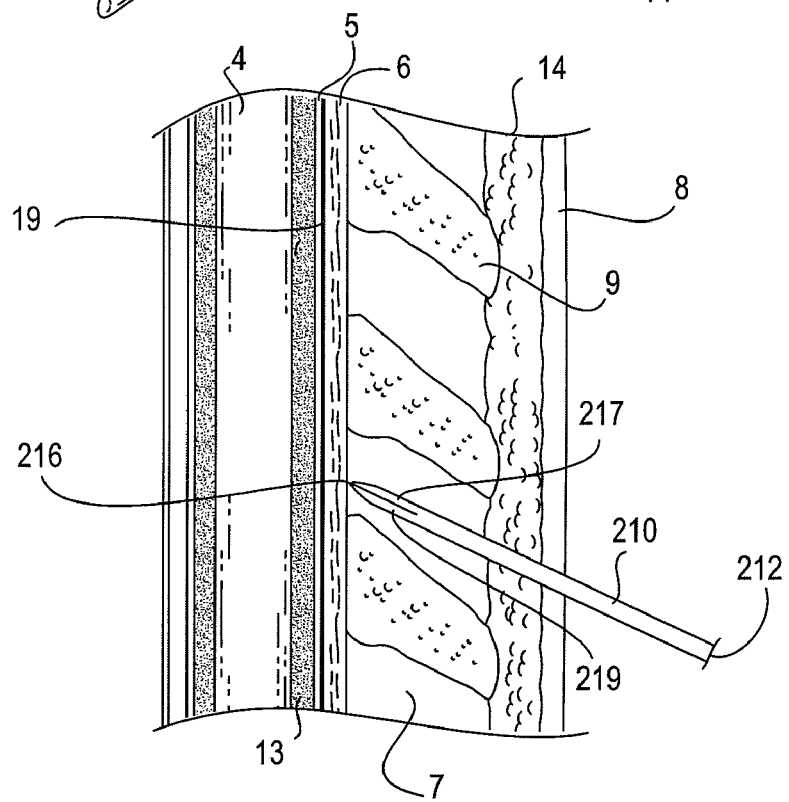
FIG. 3B is an enlarged view of FIG. 3A illustrating the position of the cutting sheath in relation to the ligamentum flavum and the surrounding anatomy.

FIG. 3B depicts a cross-sectional view of the penetration of the sheath 210 to the ligamentum flavum 6. FIG. 3B also illustrates the cutting sheath 210 in position with respect to the surrounding anatomical structures including the skin 8, underlying soft tissue 14, interspinous ligament 7, ligamentum flavum 6, epidural space 19, the dura 5, the cerebrospinal fluid 13, the spinal cord 4 and the spinous process 9. The cutting sheath 210 may or may not partially penetrate the outer surface of the ligamentum flavum 6. Positioning the cutting sheath 210 up to or partially into the ligamentum flavum 6 is achieved by stopping advancement once an increased resistance to penetration is detected when pushing to advance the cutting sheath 210 through the tissue. This increased resistance is common and relates typically to the stiffer nature of the ligamentum flavum 6 relative to surrounding soft tissues 14. At this point, the step of forming an opening to a position at or near the ligamentum flavum using a cutting sheath is completed.

Figure 4A:
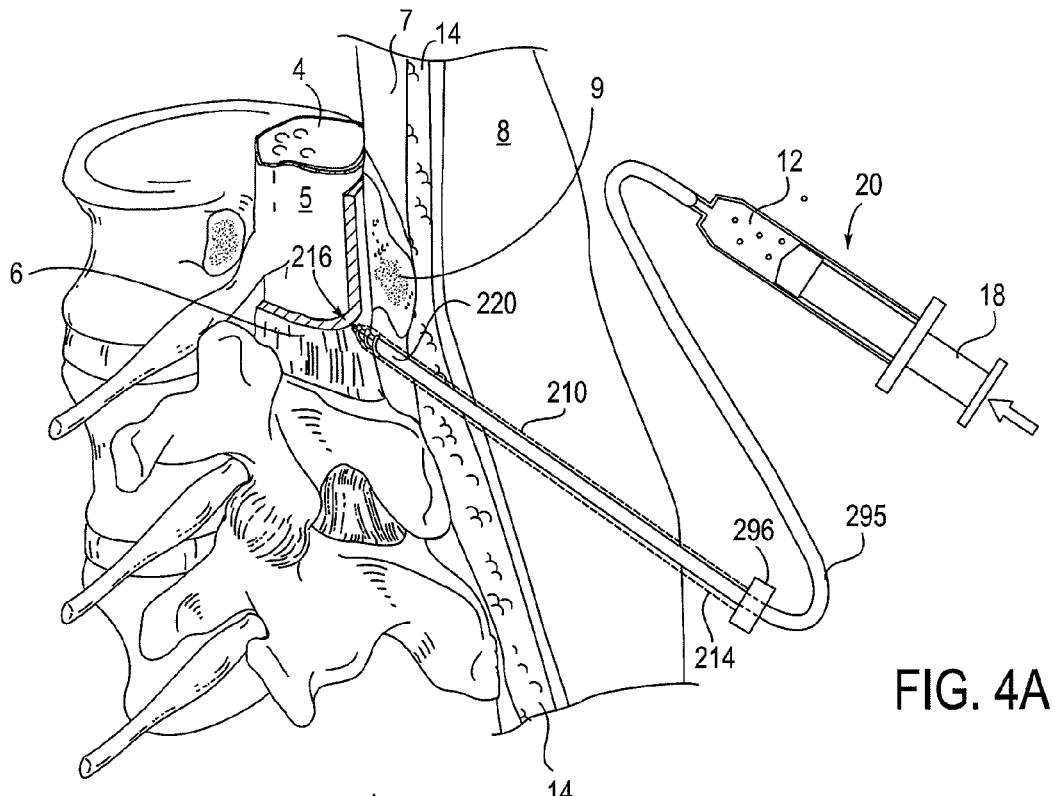
FIG. 4A is a perspective view of the cutting sheath as positioned in FIG. 3A including a tissue engagement device within the cutting sheath and a flexible line connecting a syringe to the tissue engagement device.
Figure 4B:
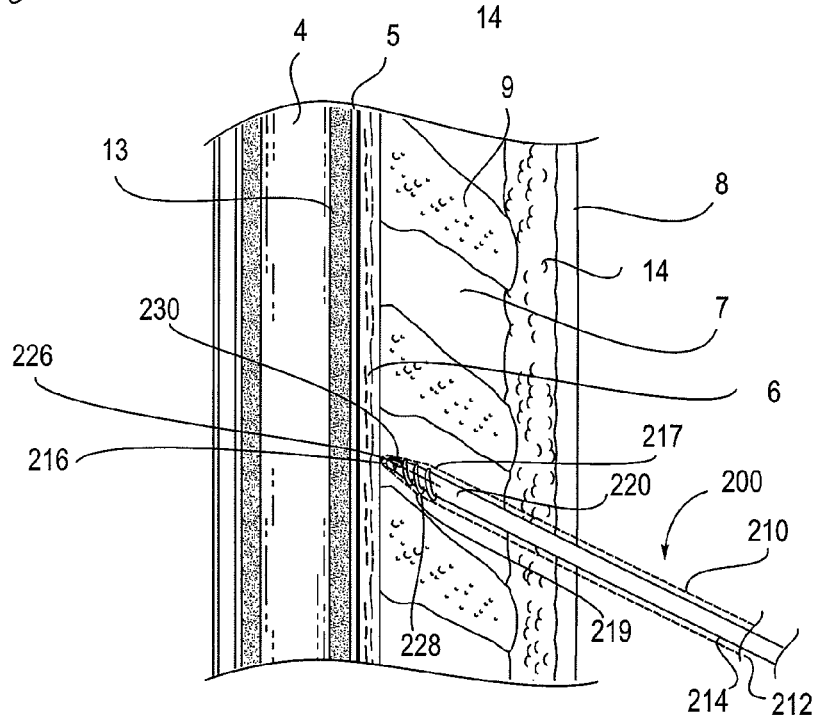
FIG. 4B is an enlarged view of the cutting sheath and tissue engagement device illustrated in FIG. 4A.

Returning to FIG. 2. The next step is positioning a blunt-tipped tissue engagement device within a hollow portion of the cutting sheath (step 120). During the forming step, the cutting sheath 210 may be used with or without the tissue engagement device inside the hollow portion 214. As such, the step of positioning the tissue engagement device may be performed before or after the step of forming an opening to the ligamentum flavum with the cutting sheath. In one aspect, the tissue engagement device is disposed within the hollow portion 214 of the cutting sheath 210 while the cutting sheath is being advanced towards and into contact with the ligamentum flavum 6. Referring to FIG. 4B, the sheath 210 is configured with a hollow interior 214 and open proximal end 212 to receive a tissue engagement device 220. FIGS. 4A-4B depict the tissue engagement device 220 within the cutting sheath in a position just outside the exterior surface of the ligamentum flavum 6. Alternatively, the cutting sheath tip 216 may be partially inserted into the ligamentum flavum 6.

Figure 4C:
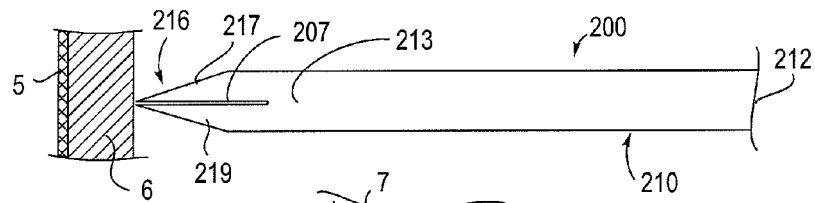
FIG. 4C is an enlarged view of the cutting sheath in FIG. 3B in a closed cutting configuration in position relative to the ligamentum flavum.
Figure 4D:
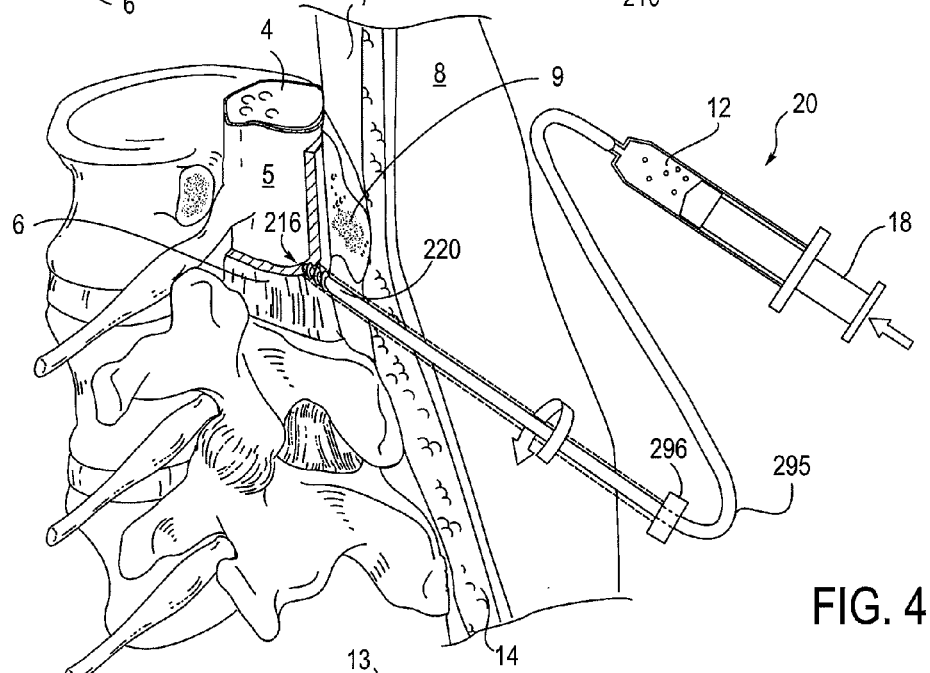
FIG. 4D is a perspective view of the cutting sheath and tissue engaging device of FIG. 4A indicating the rotation of the tissue engagement device and the transition of the cutting sheath from a closed cutting configuration to an open configuration.
Figure 4E:
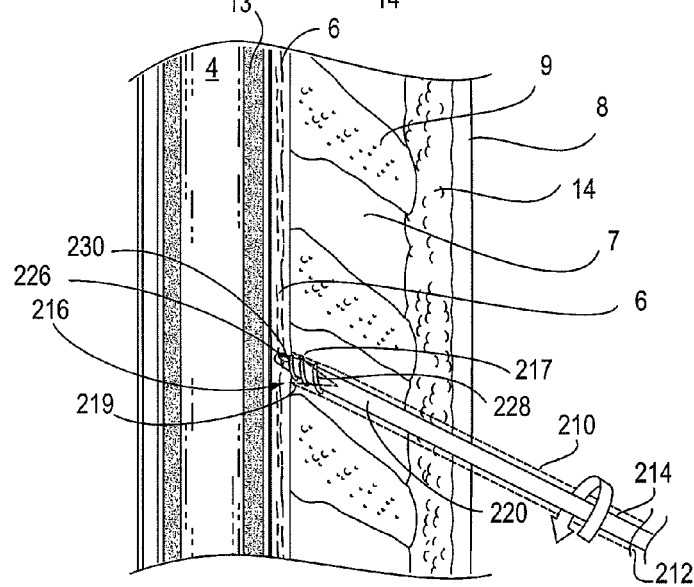
FIG. 4E is an enlarged view of the cutting sheath and tissue engagement device as positioned in FIG. 4D and the blunt end of the tissue engagement device within the ligamentum flavum.
Figure 4F:
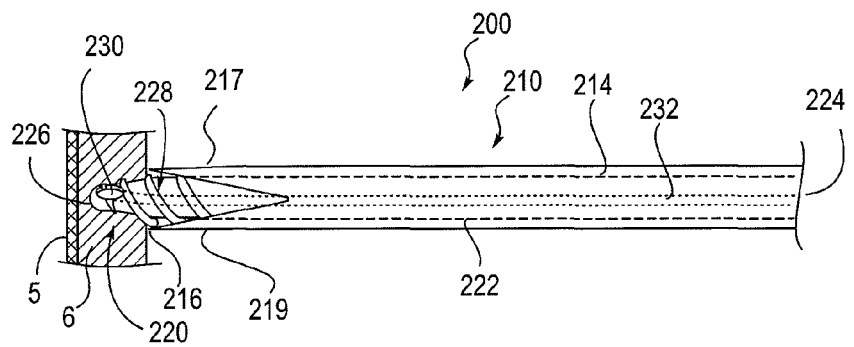
FIG. 4F is an enlarged view of FIG. 4E showing the tissue engagement device within and cutting sheath against the ligamentum flavum.

Once the tissue engagement device is in position, the next step is transitioning the distal end of the cutting sheath from a closed cutting configuration to an open configuration (step 125). This step relates to conversion of the cutting sheath 210 from a closed cutting configuration to an open configuration. Once in the open configuration, the tissue engagement device inside the cutting sheath is exposed to surrounding tissue. FIGS. 4C-4E show in detail the sheath 210 after transitioning from a closed cutting configuration to an open configuration to allow controlled advancement of the tissue engagement device 220 through the ligamentum flavum 6.

As depicted in FIG. 4C, the cutting sheath distal end 216 consists of two flaps 217, 219 separated by a small gap or separation area 207. FIG. 4E illustrates the transition of the sheath 210 from a closed cutting configuration to an open configuration when the tissue engagement device distal end 226 is advanced. As the tissue engagement device distal end 226 advances, the flaps 217, 219 deflect and separate along the predefined separation line 207. In one aspect, relative movement between the tissue engagement device and the cutting sheath is facilitated by retraction of the sheath 210 relative to the tissue engagement device 220. The sheath distal end 216 may transition between closed and open states via a number of mechanisms. One mechanism includes built in preferential separation planes similar to those formed using separation area 207. Flaps on these preferential separation planes are biased closed and remained closed without external forces acting on them. The area 213 near the proximal end of the separation area 207 may also be modified to aid in predefined movement of the distal tip. The area 213 may contain different materials, structures or be formed differently from the remainder of the sheath 210 in order to facilitate the movement of the flaps 217, 219. The area 213 may be modified so as to behave as a hinge between the flaps 217, 219 and the body of the sheath. Transition of the cutting sheath from a closed cutting configuration to an open configuration may be facilitated in a number of ways. The transition may be facilitated by retracting the sheath relative to the tissue engagement device, distal advancement of the tissue engagement device relative to the sheath distal end via rotation or direct linear translation of the tissue engagement device.

Figure 1A:
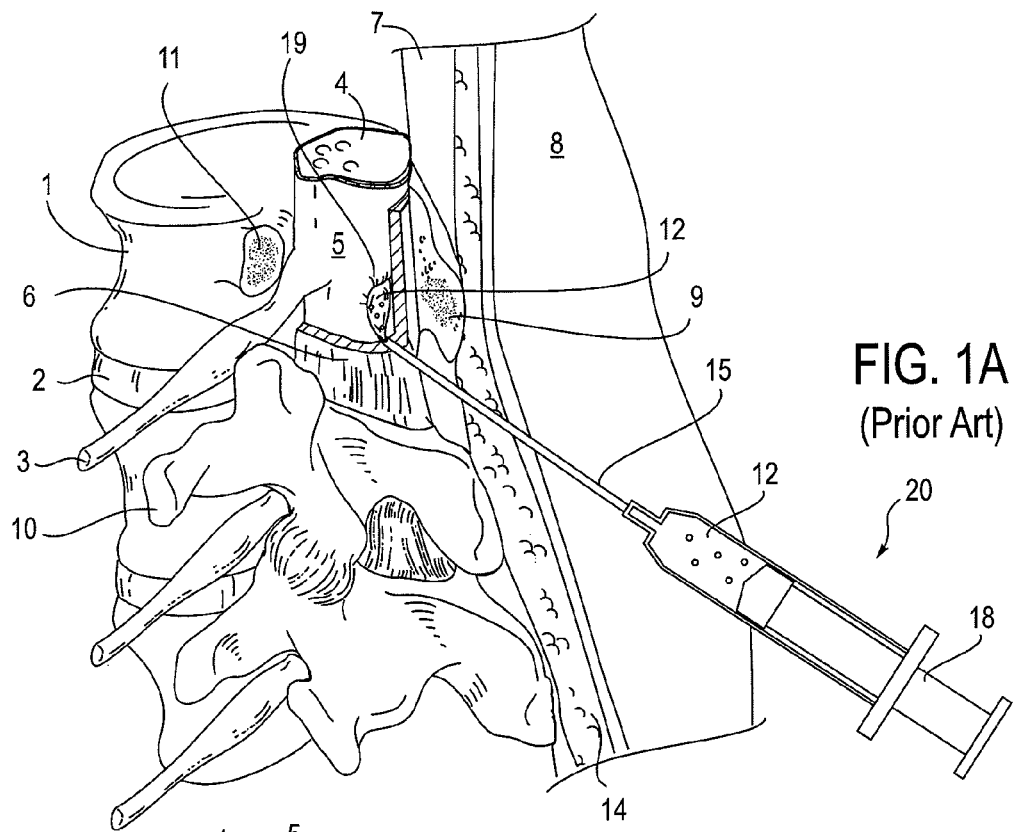
FIG. 1A is a perspective view of the epidural space and surrounding anatomical structures with a needle inserted into the epidural space.
Figure 1B:
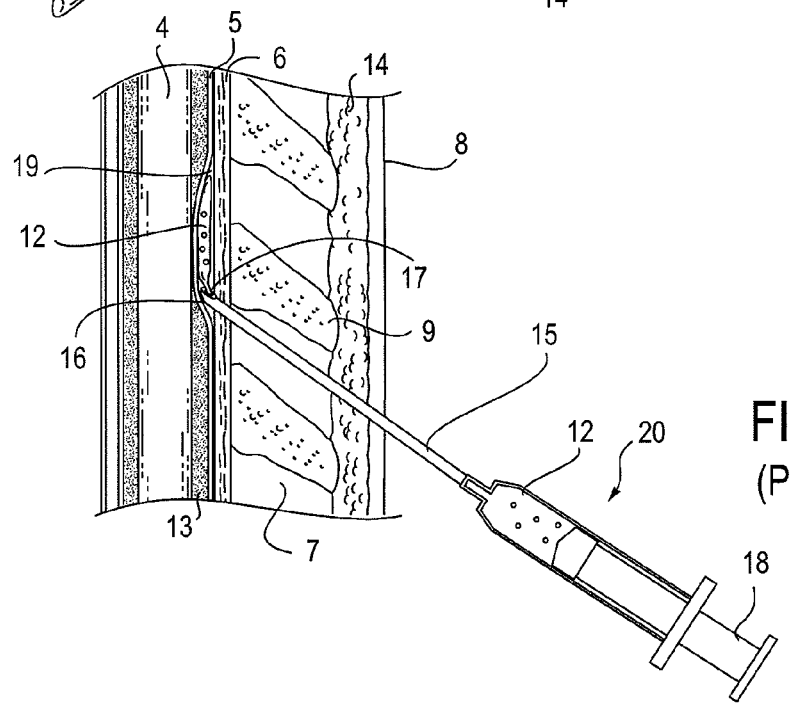
FIG. 1B is an enlarged view the epidural space of FIG. 1A showing the position of a properly placed needle tip within the epidural space.
Figure 1C:
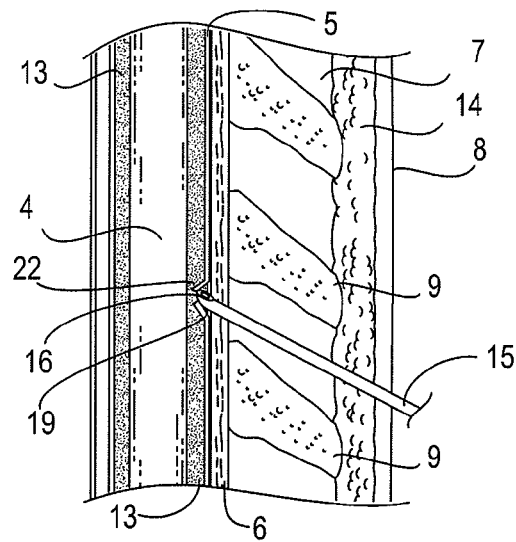
FIG. 1C is an enlarged view the epidural space of FIG. 1B showing a needle puncturing the dura.
Figure 1D:
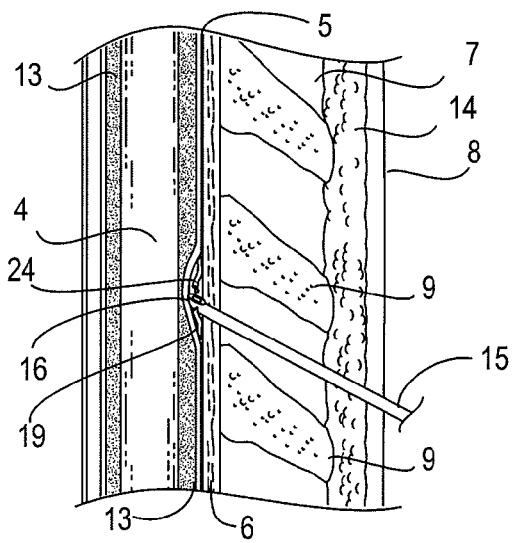
FIG. 1D is an enlarged view the epidural space of FIG. 1B showing a needle puncturing an epidural vein.
Figure 1E:
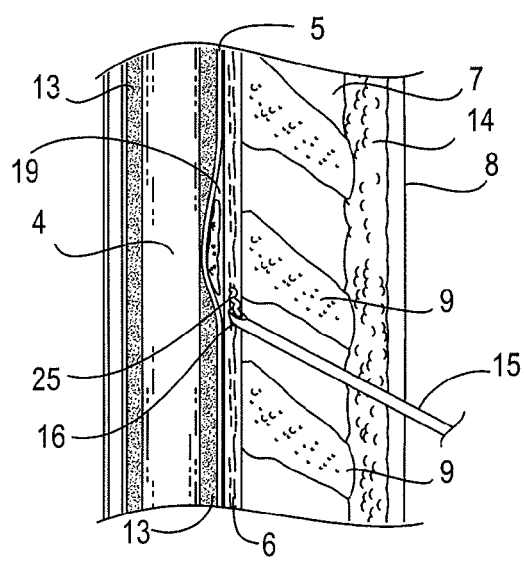
FIG. 1E is an enlarged view the epidural space of FIG. 1B showing a catheter improperly placed outside of the epidural space.

Returning to FIG. 2, the next step is manipulating an engagement feature on the tissue engagement device to controllably advance into the ligamentum flavum (step 130). After exposure of the tissue engagement device to the surrounding tissue, the tissue engagement device is manipulated to engage the ligamentum flavum. One embodiment of an engagement feature includes the use of threads 228 on the outer aspect of the distal end of the tissue engagement device to engage the ligamentum flavum and facilitate controlled advancement of the blunt tip via rotational action as depicted in FIGS. 4D, 4E. Manipulation may include any form of relative movement between the engagement features on the tissue engagement device and the ligamentum flavum. Manipulation includes, for example, rotational movement such as with a threaded form of engagement feature 228 in the tissue engagement device 220 (FIGS. 4D, 4E and 4F). The sheath is configured such that the tissue engagement device is able to rotate and/or translate within the sheath to advance through the ligamentum flavum without appreciably advancing the sheath into the ligamentum flavum. Rotation of the tissue engagement device when engaged with the ligamentum flavum facilitates translation of the threaded device through the tissue. In contrast to the purely push-to-advance method of the prior art using cutting-tipped Tuohy needles to access the epidural space, this step illustrates the transition from a push-to-advance mode to a controlled advancement mode. In this case, the advancement is controlled by controlling the rotation of the tissue engagement device. The use of one or more engagement features enables the tissue engagement device to controllably advance the blunt tip 226 through the ligamentum flavum 6. Converting the action required to advance the tissue engagement device from a push-to-advance to a threaded rotate-to-advance mode reduces the possibility of inadvertent uncontrolled forward advancement of the device that can lead to damage of critical structures (FIGS. 1C-1E). The external threads 228 secure the tissue engagement device 220 within the ligamentum flavum to provide additional protection against uncontrolled motion by increasing the linear force required to push the tissue engagement device 220 through the ligamentum flavum 6. Thread characteristics including shape and spacing may be varied to enable desired engagement and advancement characteristics. For example, a variable pitch thread may be configured to enable more coarse and rapid then finer and slower advancement of the tissue engagement device through the ligamentum flavum.

Returning to FIG. 2, the next step is to employ positive pressure on a fluid reservoir in fluid communication with an aperture on the distal end of the tissue engagement device (step 135). During controlled advancement of the tissue engagement device, the aperture 230 is within the ligamentum flavum 6 as shown in FIGS. 4D, 4E and 4F. As shown in FIG. 4D, an operator uses the well known technique of applying positive pressure to a low resistance syringe (indicated by the arrow directed to plunger 18) connected to the proximal end of the tissue engagement apparatus. As long as the aperture 230 remains in the ligamentum flavum, the operator detects a high resistance to the flow of fluid or gas 12. Embodiments of the tissue engagement devices of the present invention are adapted to allow passage of substances and devices from their proximal to distal ends using the conduit 232 and the aperture 230.

One embodiment enabling this passage involves an open proximal end of the tissue engagement device, an internal lumen enabling the air-tight passage of fluids, gases, and devices between the proximal and distal ends of the entire device and an aperture in proximity to the tip as seen in FIGS. 4A-4H. The connection between the tissue engagement device 220 and the low resistance syringe 20 may be a conventional rigid connection (FIG. 1A). Alternatively, the proximal end of the tissue engagement device terminates in a hub that allows connection to and relative rotation with a flexible tubular member 295. The hub may be a connector 296 that provides a fluid tight seal between the flexible tubing 295 and the conduit 232. The connector 296 is modified accordingly to maintain a seal depending upon the technique used to manipulate the tissue engagement device. In some embodiments, the connector 296 will be adapted to maintain a seal during longitudinal manipulation (FIGS. 12A and 12B) and in other embodiments, the connector 296 will be adapted to maintain a seal during rotational manipulation (FIGS. 4A, 4D). The hub or connector 296 may be any of a variety of conventional fluid connectors that provide the desired fluid seal. Advantageously, use of the connector 296 allows manipulation of the tissue engagement device to occur independent of the flexible tubing 295 and the syringe 20. The flexible tubular member 295 enables the operator to reduce forces that could dislodge the tissue engagement device tip, forces that would otherwise be transmitted to the tissue engagement device via a rigid connection with the syringe (FIG. 1A).

A low resistance syringe may also be incorporated into a handheld device that actuates the sheath and tissue engagement device via a flexible housing. The flexible tubular member 295 allows a operator to lie down or otherwise move the syringe or handpiece relative to the tissue engagement device without compromising the internal position of the sheath and/or the tissue engagement device. During advancement of the tissue engagement device, the remote handpiece (depicted as a syringe 20 in FIG. 4D) may include a mechanism to transmit force to the tissue engagement device for controlled advancement of the distal end of the tissue engagement device. A conventional low resistance syringe 20 or other similar device in the handpiece would ideally transmit fluid through the flexible tubing member 295 to the aperture 230 thereby providing the needed pressure feedback to confirm entry into the epidural space.

Returning to FIG. 2. The pressure sensing method is used to determine if the engagement device is within the epidural space. The operator will assess whether a pressure drop on the reservoir indicates fluid communication with the epidural space (step 145). If the operator determines that the epidural space has not been accessed, then the answer at step 145 is "NO." In this case, the operator will continue to employ positive pressure on the fluid reservoir (step 150). The operator will proceed to step 140 and continue to manipulate and controllably advance the tissue engagement device.

Once the tissue engagement device bridges the ligamentum flavum and the aperture is at least partially within the epidural space, the operator detects a significant decrease in the resistance to the flow of fluid or gas 12 as the syringe 20 empties its contents into the epidural space 19 and pushes away the dura 5 from the ligamentum flavum 6 In this case, the answer at step 145 is "YES." The operator stops advancement of the tissue engagement device (step 160).

Figure 4G:
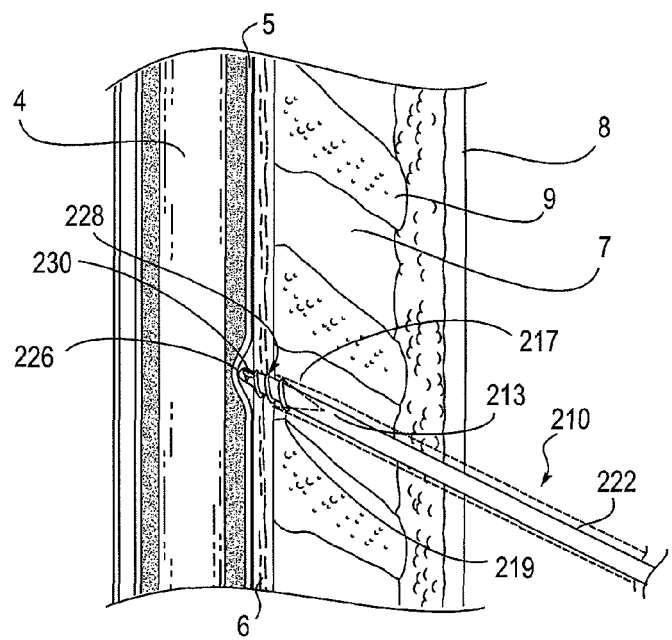
FIG. 4G is an enlarged view of the cutting sheath and tissue engagement device when the blunt end and aperture of the tissue engagement device pass through the ligamentum flavum and enter the epidural space.
Figure 4H:
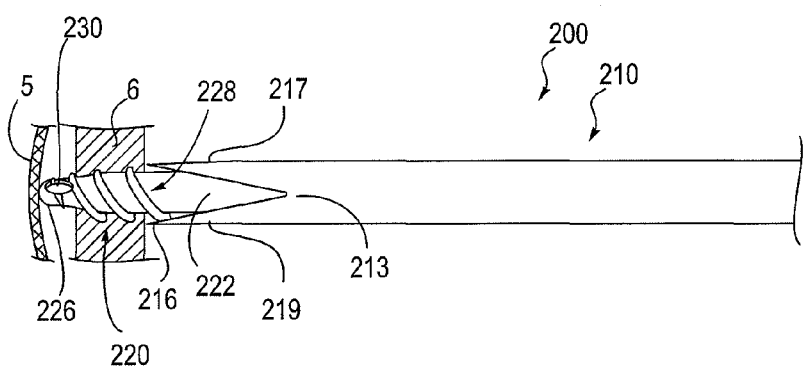
FIG. 4H is an enlarged view of FIG. 4G when the blunt end and aperture of the tissue engagement device pass through the ligamentum flavum and enter the epidural space.

A conduit is now in place between the proximal end of the tissue engagement device external to the body and the aperture 230 positioned in the epidural space 19. The blunt tip 226 is adapted to protect critical structures in and around the epidural space from being transected including the dura and epidural veins. FIGS. 4G, 4H illustrate how the blunt tip 226 better protects structures when compared to sharp-tipped needles conventionally used to penetrate the ligamentum flavum. As illustrated, the blunt tip 226 presses against the dura 5 without penetrating or piercing the structure. In one embodiment illustrated in FIG. 4H, the tissue engagement device blunt tip 226 is a rounded, conical apex configured to be sufficiently rounded to push away the dura 5 instead of transecting the tissue.

Figure 5A:
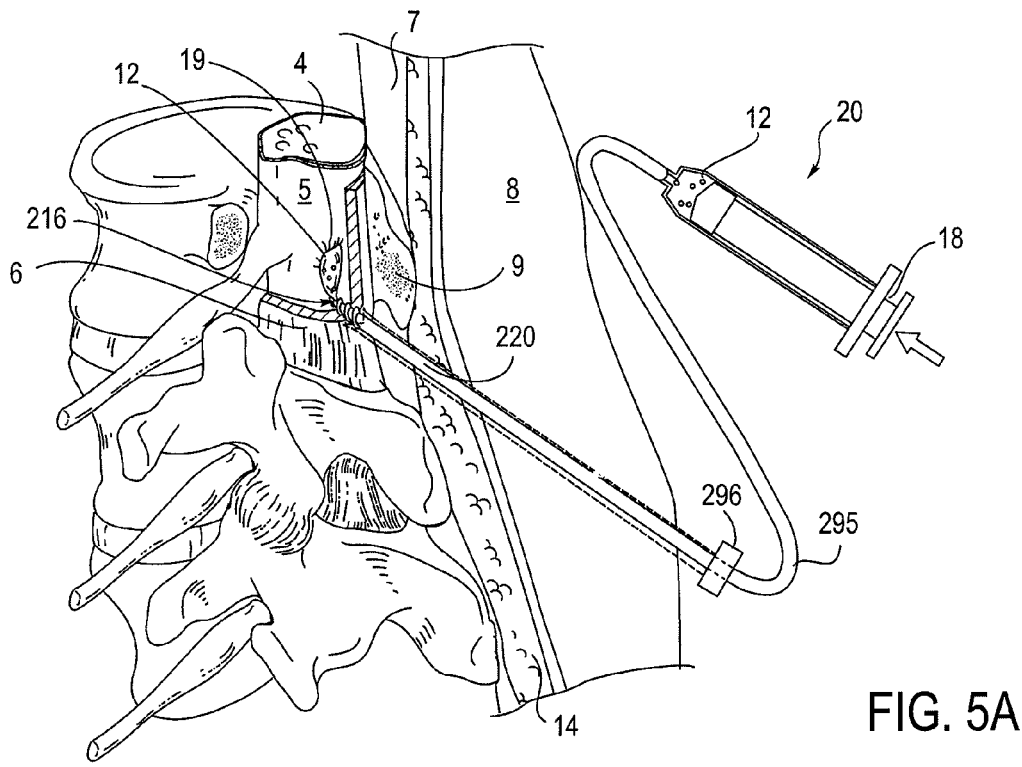
FIG. 5A is a perspective view of the cutting sheath and tissue engaging device positioned as in FIGS. 4G and 4H indicating the loss of resistance and the fluid passing into and enlarging the epidural space.
Figure 5B:
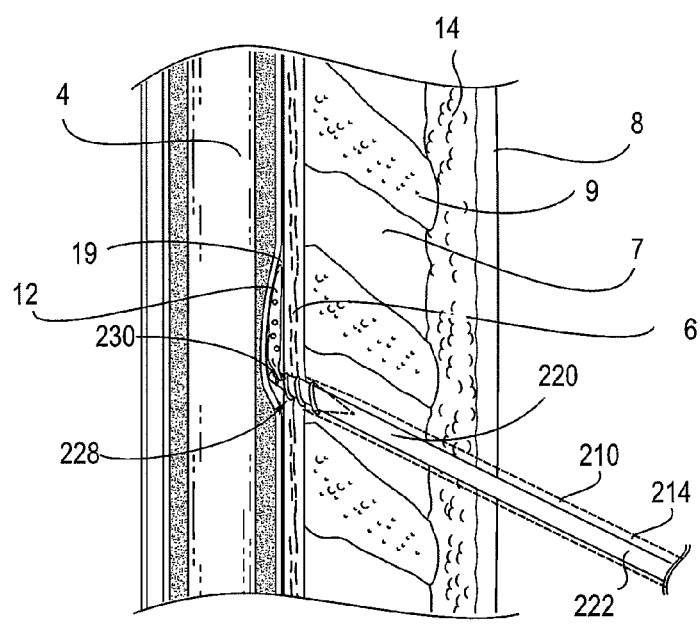
FIG. 5B is an enlarged view of the cutting sheath, tissue engagement device and epidural space of FIG. 5A.

FIGS. 5A, 5B illustrate access to the epidural space and the resultant loss of resistance indication. As compared to FIG. 4D, FIG. 5A shows the plunger 18 depressed and that the fluid 12 has moved from the syringe 20 into the epidural space 19.

FIGS. 5A, 5B, and 4H illustrate the result of advancing the device distal end 226 and aperture 230 beyond the ligamentum flavum 6. The release of gas and/or fluid 12 in the syringe 20 into the epidural space 19 results in enlargement of the epidural space 19. As seen in FIGS. 4H and 5B, the rounded distal end 226 protects against dural puncture and epidural vein puncture, and the adjacent threads 228 enable the tissue engagement device to be secured within the ligamentum flavum 6.

Figure 6A:
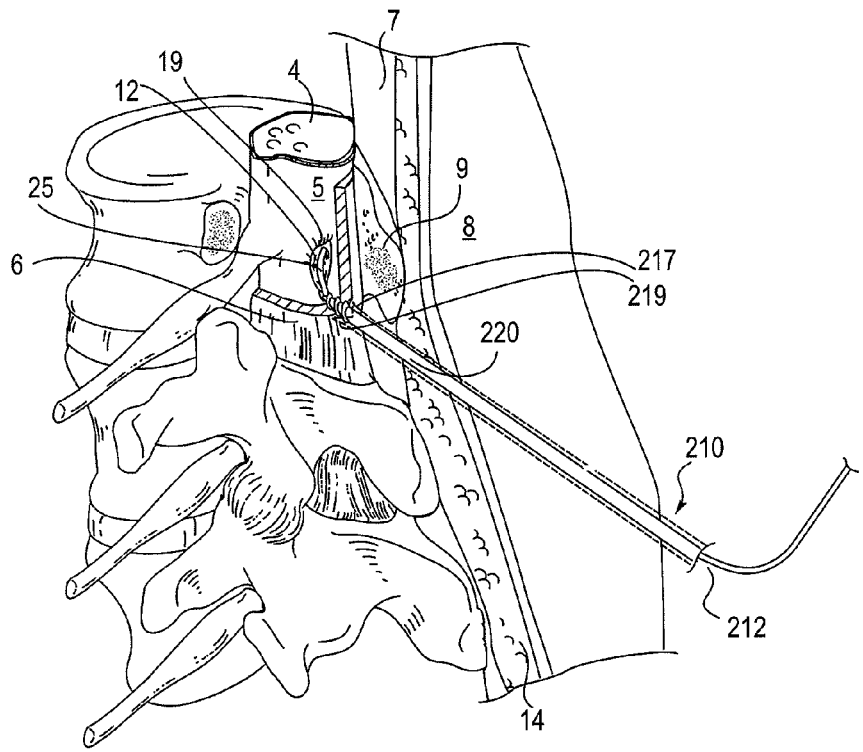
FIG. 6A illustrates a catheter being inserted into the epidural space using the tissue engagement device positioned as shown in FIGS. 5A and 5B.
Figure 6B:
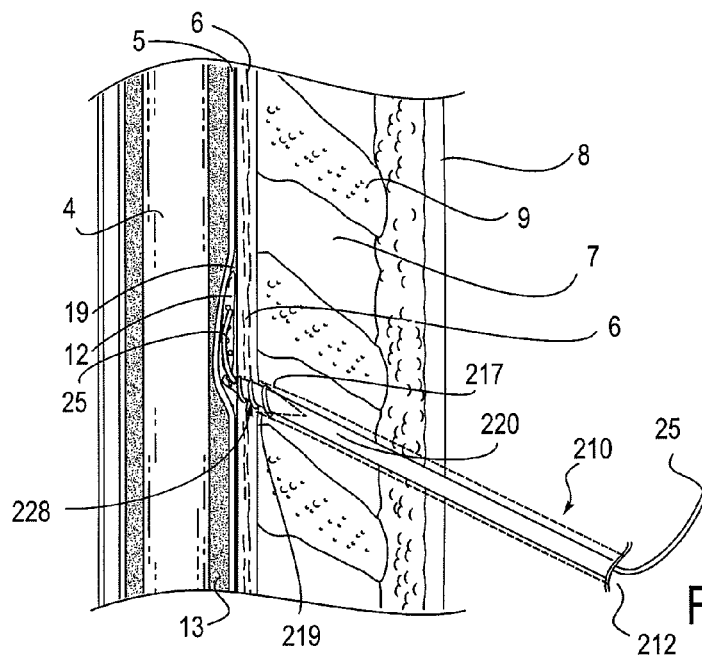
FIG. 6B is an enlarged view of FIG. 6A illustrating the catheter inserted into the epidural space.

Once access to the epidural space has been established, an operator may use the conduit and the aperture of the tissue engagement to deliver devices or therapy to the epidural space. For example, an operator may thread a catheter through the tissue engagement device and into the epidural space (step 170). FIGS. 6A and 6B illustrate the advancement of a catheter 25 through the tissue engagement device 220 and into the epidural space 19. Devices, such as electrode leads or other devices that may have an effect on structures accessible via the epidural space, may be delivered via the tissue engagement device and left in the epidural space. Generally, the diameter of the conduit 232 between the proximal end 224 to the aperture 230 in the tissue engagement device is determined by the medication or device to be delivered with typical values in the vicinity of 1 mm when conventional epidural catheters are delivered.

Figure 7A:
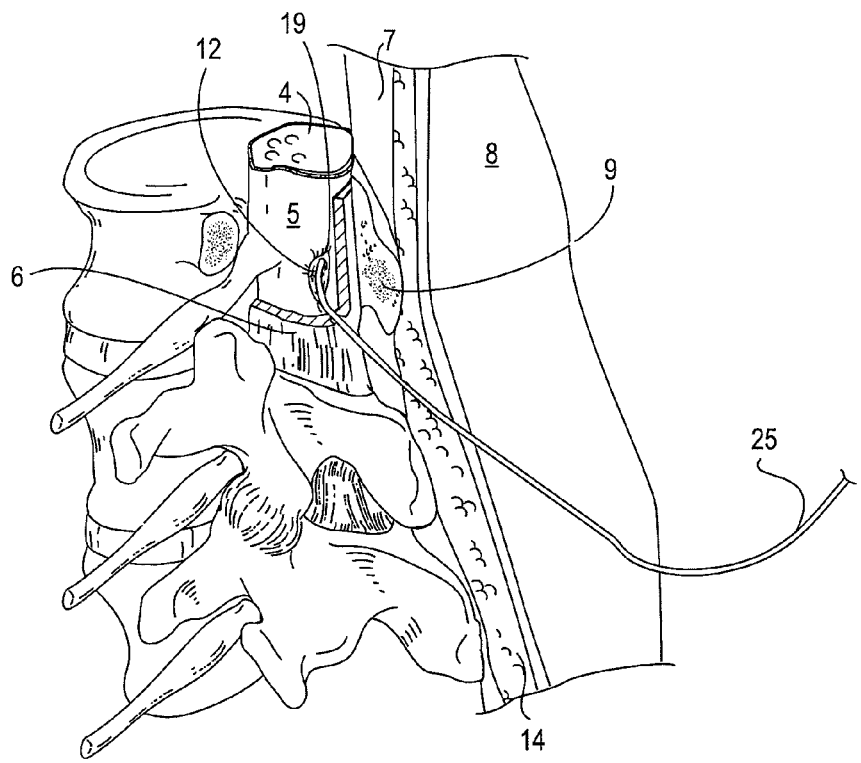
FIGS. 7A and 7B are, respectively, perspective and enlarged views of a catheter remaining in the epidural space after the removal of the cutting sheath and the tissue engagement device.
Figure 7B:
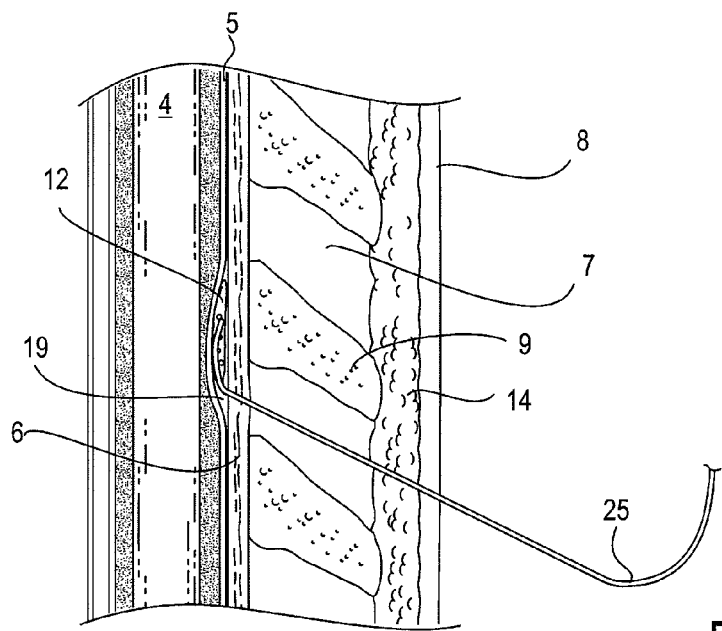

Thereafter, the cutting sheath and tissue engagement device can then be removed, leaving the catheter in place within the epidural space (180). Mechanisms suited for the withdrawal of the sheath and/or the tissue engagement device include, without limitation, a rotate-to-retract mode or a pull-to-retract mode. FIGS. 7A and 7B illustrate the final condition after removal of the sheath and tissue engagement device. The result is a catheter 25 safely inserted into the epidural space 19 using embodiments of the inventive devices and methods described herein.

Finally, if an epidural catheter 25 or other device is left in place, therapy such as continuous administration of local anesthetic can commence (step 190).

Standard helical threads are illustrated and described as the engagement feature 228 on the tissue engagement device 220 described above. However, the illustrated engagement features of the present invention are not intended to be limiting. Other thread shapes, sizes, varieties, and configurations may be used. Moreover, it is believed that certain thread configurations may provide greater control during insertion and controlled advancement while remaining easy to withdraw from the engaged tissue. For example, variations in thread form tip sharpness allow engagement of the surrounding tissue by cutting into the tissue to varying degrees. The spacing of the threads further dictates how the device engages with surrounding tissue. A small spacing may not allow the tissue to sufficiently deform between the threads leading to poor engagement. However, if the spacing is too great, there will not be a sufficient number of threads in the tissue to drive the blunt tip through the ligamentum flavum.

For satisfactory operation thread spacing or pitch must also be tempered by desired advancement characteristics in which the device can be advanced efficiently with few rotations to allow for sufficiently rapid epidural space access while maintaining appropriately fine control to not damage critical structures in the device vicinity such as epidural veins and the dura. The thread pitch ideally allows device advancement through the ligamentum flavum with minimal rotations while enabling fine control once in the epidural space. The thread may be configured with a variable pitch to enable larger and smaller increments of advancement with rotation. For example, the thread form toward the tissue engagement device tip may have a larger pitch than that more distal from the tip allowing for rapid insertion then more fine control with rotation once farther into the ligamentum flavum.

Thread height and/or overall device diameter can be similarly varied along the length of the distal end to enable larger engagement force of surrounding tissue with larger device diameter. For a given thread height, the thread pitch can be specified by adjusting the thread form angles or by adjusting spacing of a fixed thread shape and incorporating a spacing between the threads. The threads may also be right-handed or left-handed depending on desired operation characteristics.

The overall thread form further plays a significant role in the operation characteristics of the apparatus. The shape of the overall thread in addition to the thread tip affects the operational characteristics of the device. When engaging tissue, the threads generally resist linear push-to-advance motion of the tissue engagement device. The degree to which the threads resist such motion can be dictated by their shape. One thread form has been described with regard to engagement features 228 above. Another exemplary thread form is depicted in FIGS. 8A, 8B, and 8C. As best seen in FIG. 8C, a single section view of a thread shape 328 is illustrated. This view presents a thread tip 309, leading face 308, and a trailing face 306. The orientation of the leading face 308 relative to the longitudinal axis of the engagement device is defined by the leading face angle $\beta$. Similarly, the orientation of the trailing face 306 relative to the longitudinal axis of the engagement device is defined by the trailing face angle $\alpha$.

Gently sloping thread forms are defined by larger angles $\alpha$ and $\beta$. In general, gently sloping thread forms result in lower forces required for linear advancement. In the case of symmetric thread forms, the force required for linear advancement of a tissue engagement device is similar to the force needed for linear retraction of a tissue engagement member. For example, a symmetric thread form may be designed to resist both forward and reverse linear motion of the engagement device in the tissue. The threads may be designed to resist inadvertent motion in the ligamentum flavum due to typical linear forces encountered during device advancement by the operator. The threads additionally may be configured to reduce such motion when forces beyond the typical range are encountered. Such a design allows the ligamentum flavum to tend to be pulled away from the dura during device advancement with rotation and application of a pulling force, providing additional protection against damage to the dura during entry into the epidural space. Asymmetric thread forms can skew this symmetry in linear advancement or retraction force and enable greater resistance to forward linear advancement and lower resistance to linear retraction of the tissue engagement device. Departures from symmetry involve variations in the shapes of each thread face including different curvatures and angles, for example. For straight-edged thread forms trailing and leading angles $\alpha$ and $\beta$, respectively, with different values can result in a tissue engagement device having linear advancement characteristics different from its linear retraction characteristics. For example, the threads could be configured such that the force required to advance the tissue engagement device with linear force is significantly greater than that required to linearly retract the device, providing an added measure of safety for structures in front of the engagement device and ease of simple pull-to-retract device withdrawal. In such a case, the trailing edge angle, $\alpha$, would be specified greater than the leading edge angle, $\beta$, to enable lower forces during pull-to-retract withdrawal of the tissue engagement device compared to forces that would be required to push-to-advance the device. The more gently trailing edge can also reduce tissue trauma by allowing the engaged tissue to deform more gradually as the device is linearly retracted as depicted in FIG. 8C.

One embodiment of a threaded engagement mechanism with an asymmetric thread form is the reverse buttress thread form depicted in FIGS. 8A, 8B and 8C. The cross-sectional views of the engagement features 228 depict a reverse buttress thread form with a standard leading face angle β of 90° and a trailing face angle α of 150°. The asymmetric thread shape of the reverse buttress design resists push-to-advance forces when advancing the engagement device toward the epidural space. At the same time the sloped geometry of the trailing face facilitates lower tissue resistance to pull-to-retract forces. The main advantage of this configuration is that it allows the apparatus to be directly pulled out of the ligamentum flavum, similar to conventional methods, rather than requiring rotation of the device to disengage the ligamentum flavum.

Symmetric thread forms with heights between 0.1-0.27 mm have been demonstrated to provide good tissue engagement properties in the ligamentum flavum. Spacing between thread forms in the range of 0.1-0.2 mm have demonstrated desirable tissue engagement characteristics. It is believed that leading face angles, β, less than 120° would provide further increased resistance to linear translation. It is also believed that trailing face angles, α, greater than 120° would provide reduced resistance to linear retraction.

FIGS. 9A and 9B illustrate an apparatus 400 for accessing the epidural space. The apparatus 400 includes a cutting sheath 410 and a tissue engagement device 420 within the sheath 410. The cutting sheath 410 includes a distal end 416 divided into multiple sections three of which are visible in FIG. 9A. The sections 417, 418 and 419 are separated by score lines 417a and 418a. As with previous embodiments of epidural access devices, a tissue engagement device is within the cutting sheath. FIG. 9B illustrates the cutting sheath 410 in an open configuration with the blunt tip 426 of the tissue engagement device 420 in the epidural space 19 and in non-penetrating contract with the dura 5. The tissue engagement device 420 includes threaded engagement elements 428, an aperture 230 and other features as described with previous tissue engagement device embodiments.

In contrast to the cutting sheath in FIG. 4, FIGS. 9A and 9B depict an alternative sheath distal end design with a closed cutting configuration that is completely closed. In FIG. 4C the flaps on the distal end of the sheath are separated by a small slot cut into the device, and the closed cutting configuration is adapted to preclude the tissue engagement device from moving beyond the distal end of the sheath. However, depending on the configuration the small spacing between the flaps may allow a small amount of tissue to enter the sheath during penetration. Alternatively, the flaps 217 and 219 may also be biased closed in a manner that prevents tissue from entering the sheath such as by overlapping the flap edges. Returning to FIG. 9, as before, the open configuration (FIG. 9B) is adapted to allow the tissue engagement device 420 to pass beyond the distal end of the sheath 416 exposing the tissue engagement device 420 to the ligamentum flavum 6. The blunt end 426 deflects but does not penetrate the dura 5 as shown in FIG. 9B. FIG. 9A illustrates a closed configuration adapted to prevent passage of tissue into the inner hollow compartment of the sheath. The sheath is then configured to open in a predetermined manner using a number of smaller flaps (i.e., flaps 417, 418 and 419) that are preferentially separate along predefined score lines 417a, 418a which may be on the exterior of the sheath as depicted in FIG. 9A. Alternatively, the score lines may be located on the interior surface of the sheath so that a smooth exterior surface is presented to the tissue during penetration. Optionally, score lines may be present on both or either of the sheath interior and exterior surfaces. As the flaps 417, 418, and 419 open, they may bend and deflect open as shown or rotate about naturally occurring hinges that arise due to the mechanical deformation of the sheath. Living hinges may also be incorporated into the sheath distal end to define locations about which the distal flaps will rotate. Such movements may be providing using the properties described above for the modified area 213 in sheath 210.

FIGS. 10A and 10B illustrate an apparatus 500 for accessing the epidural space. The apparatus 500 includes a cutting sheath 510 and a tissue engagement device 420 within the sheath 510. The cutting sheath 510 includes a distal end 516 having at least one movable flap. In the embodiment illustrated in FIG. 10A, the movable flap is flap 517. The movable flap 517 is configured to move relative to flap 519 and the distal end 516. In other embodiments, both flaps 517, 519 may be configured to move. As with previous embodiments of epidural access devices, a tissue engagement device is within the cutting sheath 510. FIG. 10B illustrates the cutting sheath 510 in an open configuration where the movable flap 519 has moved to transition the distal end of the sheath 510 to an open configuration. Also shown in FIG. 10B, the blunt tip 426 of the tissue engagement device 420 is in the epidural space 19 and in non-penetrating contract with the dura 5. The tissue engagement device 420 includes threaded engagement elements 428, an aperture 230 and other features as described with previous tissue engagement device embodiments.

FIGS. 10A and 10B depict still another alternative sheath distal end designed to predictably open with tissue engagement device advancement. The distal end preferentially remains closed during insertion due to the configuration of the flap 517. The flap 517 may be biased closed or preferentially separate along defined lines with advancement of the tissue engagement device through the distal end of the sheath similar to the modes utilizing score lines described above with regard to FIGS. 9A, 9B. The asymmetrical shapes of flaps 517, 519 can further facilitate steering of the device distal end 516 by rotating the body of the sheath 510 in a technique similarly performed with conventional Tuohy needles. During tissue engagement device advancement, the flap 517 opens by deflection as illustrated. The flap 517 rotates about a naturally forming hinge due to the mechanical properties of the sheath material, or, alternatively, a built-in living hinge.

Figure 11A:
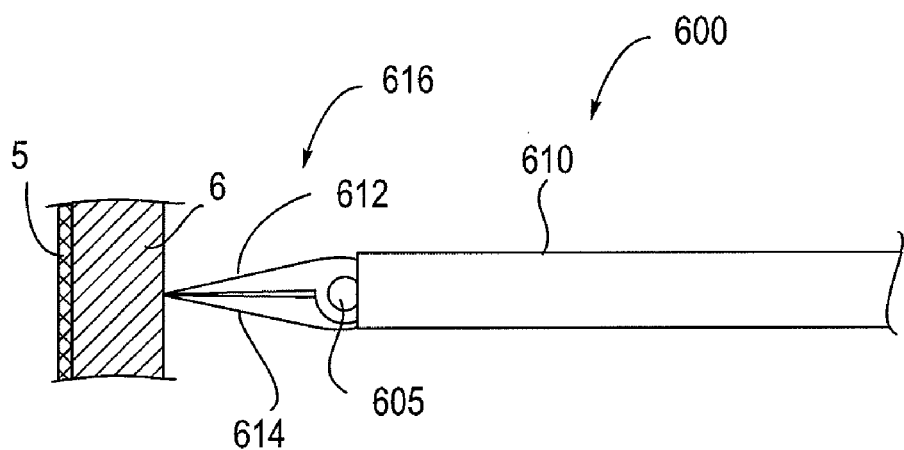
FIGS. 11A and 11B illustrate an apparatus for accessing the epidural space.
Figure 11B:
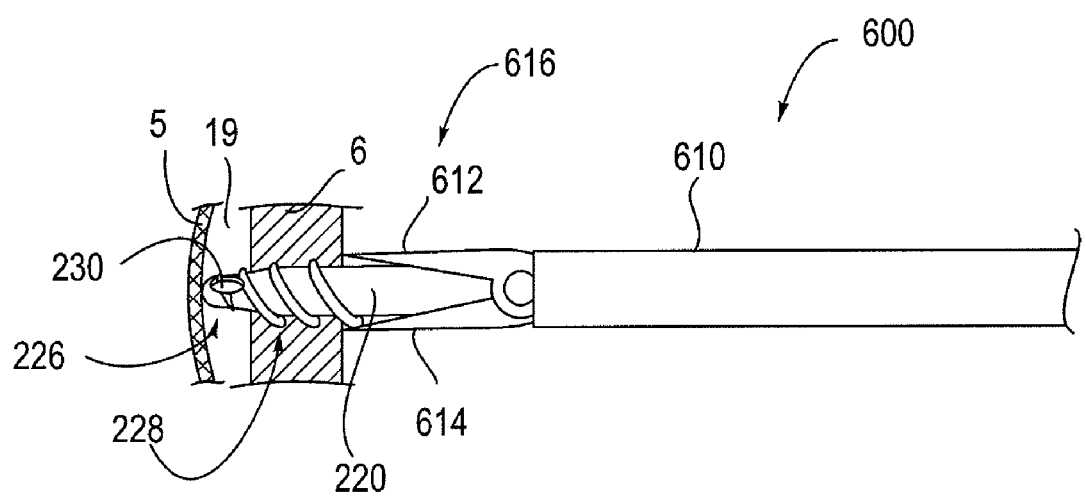

FIGS. 11A and 11B illustrate an apparatus 600 for accessing the epidural space. The apparatus 600 includes a cutting sheath 610 and a tissue engagement device 220 within the sheath 610. The cutting sheath 610 includes a distal end 616 having at least one predefined movable section that may rotate about a hinge. In the embodiment illustrated in FIG. 11A, the distal end 616 is divided into sections 612, 614. A hinge 605 is positioned proximal to the distal end 616. Depending upon the configuration of the sections 612, 614 and the hinge 605, one or both of the sections 612, 614 may be a movable section. As with previous embodiments of epidural access devices, a tissue engagement device is within the cutting sheath 610. FIG. 11B illustrates the cutting sheath 610 in an open configuration where the movable sections 612, 614 have moved to transition the distal end of the sheath 610 to an open configuration. Also shown in FIG. 11B, the blunt tip 226 of the tissue engagement device 220 is in the epidural space 19 and in non-penetrating contract with the dura 5. The tissue engagement device 220 is described above.

FIGS. 11A and 11B depict another manner of allowing the sheath distal end to transition from a sharp cutting configuration to an open configuration wherein the distal end of the sheath opens a least one predefined movable section about a hinge mechanism. The device described herein alters its configuration to facilitate a different mode of advancing through tissue. In this embodiment the apparatus transitions from a cutting or penetrating push-to-advance mode to a controlled advancement mode via opening of the sheath tip comprising movable components about a hinge at the distal end of the sheath. The hinge may be a mechanical hinge as depicted in FIG. 11A. In this embodiment the hinge 605 is incorporated into the sheath distal end and may be actuated externally or by manipulation of the tissue engagement device to cause the hinge to open as illustrated in FIG. 11B. The initial configuration of the hinge as shown in FIG. 11A shows two movable sections separated by a small space. The movable components at the sheath distal end 616 may also be closed in such a manner without such small openings, preventing tissue from entering the sheath. Alternatively, the movable components may start in a closed cutting configuration that is completely closed. The movable components may be defined by score lines on the internal or external surface of the sheath or a combination of the two. The separation of the movable components would then occur with actuation of the hinge 605 or passive separation of the movable components by advancing the internal tissue engagement device.

The step of manipulating an engagement feature on the tissue engagement device to controllably advance through the ligamentum flavum may take on any number of different forms. Threading and rotational manipulation have been described but other forms of manipulation are possible. Another form of manipulation includes longitudinal relative movement between the engagement features on the tissue engagement device and the ligamentum flavum. The longitudinal aspect of the manipulation refers to movement of the tissue engagement device relative to the longitudinal access of the device.

Figure 12A:
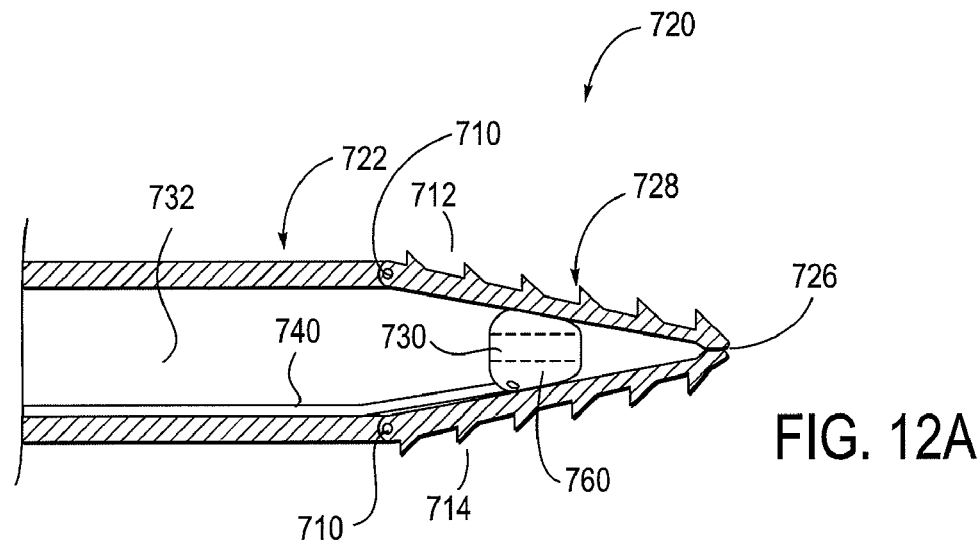
FIGS. 12A and 12B illustrate a section view of a hinged tissue engagement device.
Figure 12B:
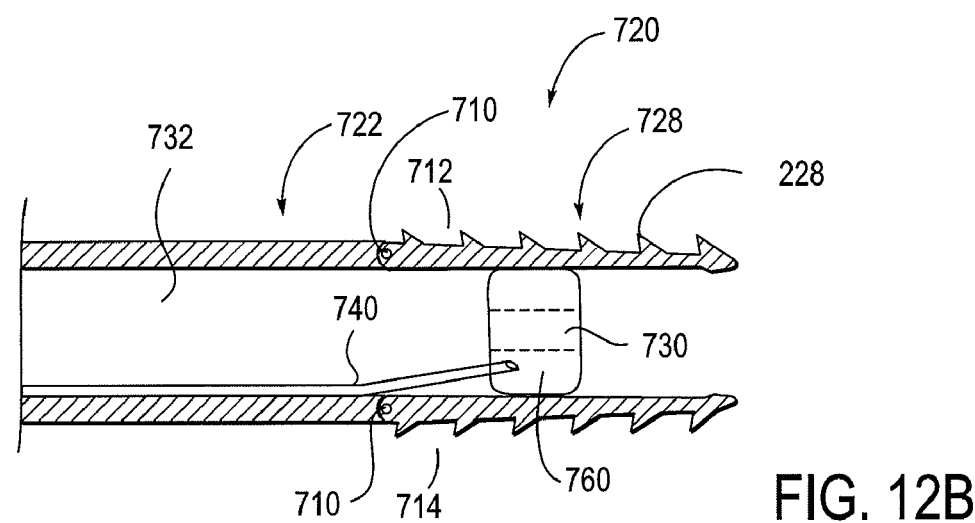

FIG. 12A illustrates a tissue engagement device 720 with the hinged distal end in a closed condition. The tissue engagement device 720 is one example of a device that utilizes longitudinal movement for controlled advancement through the ligamentum flavum. The tissue engagement device 720 includes an elongated body 722, a blunt distal end at 726 and a conduit 732. While other embodiments of the tissue engagement device 720 may be provided with a single movable section and hinge, an embodiment having two movable sections 712, 714 each with a hinge 710 is illustrated in FIGS. 12A and 12B. A hinge 710 allows a movable section to move in such a fashion that the engagement features 728 engage the ligamentum flavum. In the illustrated embodiment, the two moving sections 712, 714 are attached to the elongated body 722 by hinges 710.

A plurality of tissue engagement features 728 are positioned along the moving sections 712, 714. In the illustrated embodiment, the engagement features 728 are ridges or teeth. The shape, size and orientation of the engagement features 728 is selected to engage with the tissue of the ligamentum flavum when the distal end is expanded as shown in FIG. 12B.

An expansion element is disposed within the conduit 732 for the purpose of moving the movable sections 712, 714 from a closed position (FIG. 12A) to an open position (FIG. 12B). The at least one hinge proximal to the ridges 728 allows sections 712, 714 at the tip of the device to move in such a fashion that the ridges 728 engage in the ligamentum flavum to grasp and dissect apart the ligamentum flavum at the distal end of the device as well as form an opening ahead of the tip to create a pathway through the ligamentum flavum. In one embodiment, the expansion element lies at least partially distal to the hinge 710 in order to control the lateral extension of the one or more movable sections 712, 714. After each dissecting action, the sections 712, 714 flaps can then be repositioned in a closed manner as seen in FIG. 12A, the device advanced into the newly created opening in front of the device tip, and actuated again to open and dissect additional tissue as shown in FIG. 12B.

In the embodiment illustrated in FIGS. 12A, 12B, the expansion element is a balloon 760. The balloon 760 is attached to an interior surface of the moving sections 712, 714 in such a way that when the balloon 760 is inflated the movable sections 712, 714 rotate about their respective hinges 710. The balloon 760 facilitates actuation of the movable flaps by inflating and deflating to change between open and closed modes. The balloon 760 also includes a lumen or aperture 730 that allows communication between the conduit 732 and the distal end of the device. A second conduit 740 connects the balloon 760 and an inflation source (not shown). During use, the operator would change balloon 760 inflation to control the amount of movement of the movable sections 712, 714. FIG. 12B illustrates the tissue engagement device 720 in an open condition where balloon 760 is inflated and the movable sections 712, 714 are separated. Deflating the balloon 760 returns the tissue engagement device 722 to the condition shown in FIG. 12A.

The aperture in the device enables use of the familiar epidural space access detection technique of applying pressure to a fluid or gas filled syringe during advancement with the operator detecting a significant decrease in the resistance to the flow of fluid or gas as the syringe empties its contents into the epidural space. Once in the epidural space, a device can be placed through the device similar to the tissue engagement device embodiments described earlier. The lumen 730 in the balloon allows fluid or gas passage for epidural space access detection as well as delivery of desired medications, catheters, or other devices into the epidural space. For added protection of critical structures such as the dura and epidural veins, the distal tips of the engagement device present blunted surfaces to contacted tissue structures during operation as depicted in FIGS. 12A and 12B.

Figure 13:
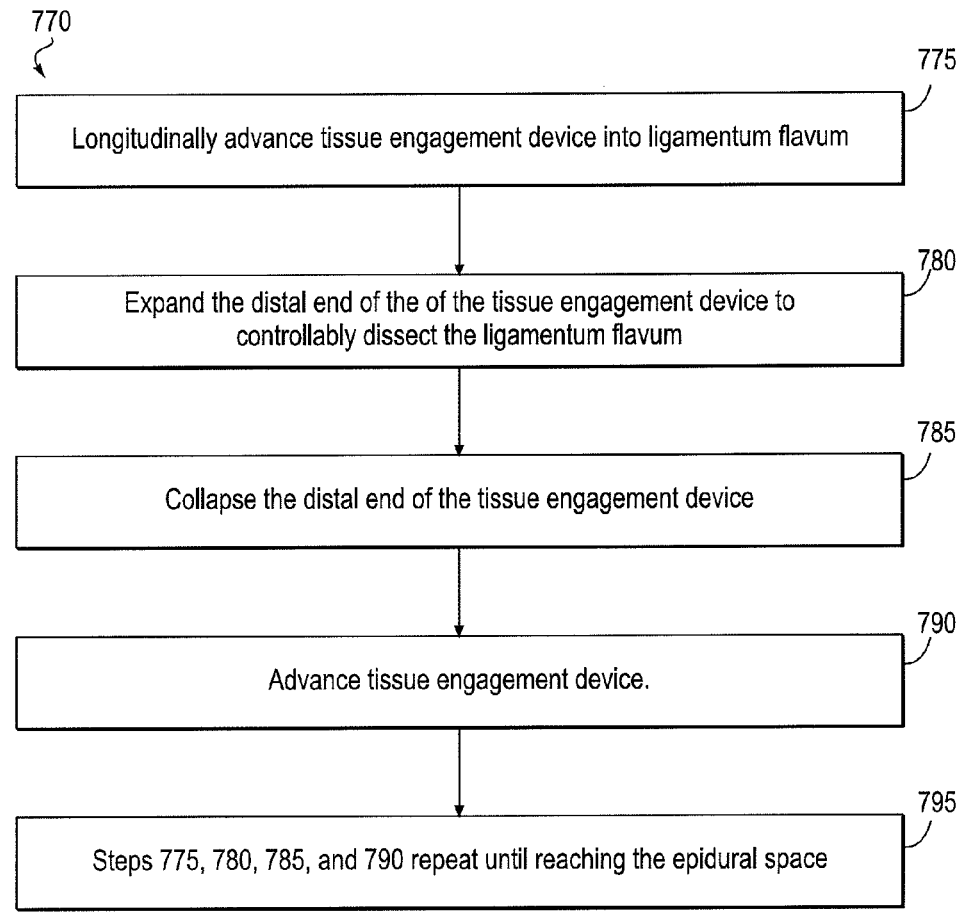
FIG. 13 is a flow chart of a method of using the tissue engagement device of FIGS. 12A and 12B.

FIG. 13 is a flow chart 770 that describes an alternate technique for the manipulation of the tissue engagement device 720 for controlled dissection of and advancement through the ligamentum flavum. First, at step 775, longitudinally advance the tissue engagement device 720 into the ligamentum flavum. This step is performed while the tissue engagement device 720 is in the closed condition as illustrated in FIG. 12A. Next, at step 780, expand the distal end of the of the tissue engagement device to controllably dissect the ligamentum flavum. This step is performed by inflating the balloon 760 to move the movable sections 712, 714 to the open condition illustrated in FIG. 12B. Next, at step 785, collapse the distal end of the tissue engagement device. This step is performed by deflating the balloon 760. As the balloon 760 deflates, the moving sections 712, 714 are brought back together to the closed condition illustrated in FIG. 12A. Next, advance the tissue engagement device (step 790). Finally, at step 795, steps 775, 780, 785 and 790 repeat until reaching the epidural space. The operator will alternately inflate and deflate the balloon 760 in conjunction with incremental advancement of the tissue engagement device 720 until reaching the epidural space. Detection of the epidural space using the loss-of-resistance technique and the placement of devices or therapy into the epidural space would then follow as described above.

As described in the embodiments above, the closed cutting configuration of a cutting sheath may be provided in a number of ways. Still another way of providing a closed cutting configuration is to occlude a normally open cutting sheath. Occlusion of the normally open cutting sheath may take many forms. For example, a stylet or a tissue engagement device placed into the hollow portion of the sheath could provide the occlusion. Accordingly, there is another alternative apparatus for accessing the epidural space in a mammal by providing a cutting sheath having an open proximal end and a distal end adapted to transition from a closed cutting configuration to an open configuration. The cutting sheath has a hollow portion extending from the open proximal end to the distal end. In one aspect, a stylet is placed within the hollow portion when the cutting sheath is in the closed cutting configuration, and a tissue engagement device disposed within the hollow portion when the cutting sheath is in the open configuration. In another aspect, a tissue engagement device is disposed within the hollow portion of the sheath to provide the closed configuration and then, when advanced from the sheath, provides for the transition to an open configuration.

Figure 14:
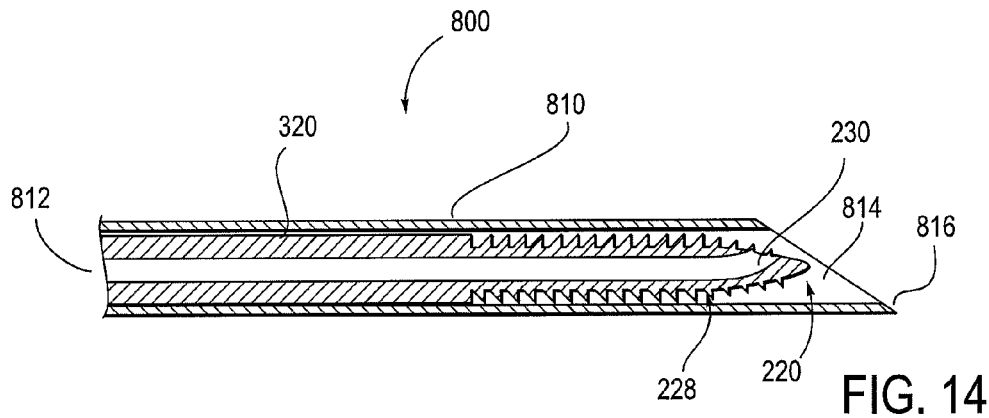
FIG. 14 is a section view of an apparatus for accessing the epidural space that has a cutting sheath and a tissue engagement device within the cutting sheath.

One such apparatus that demonstrates the use of occlusion to provide a closed cutting configuration is the apparatus 800 illustrated in FIG. 14. The apparatus 800 includes a cutting sheath 810 having a distal end 816, an open proximal end 812 and a hollow portion 814 extending there between. FIG. 14 illustrates the case where a tissue engagement device 220 is positioned within the hollow portion 814 to place the cutting sheath 810 in a closed cutting condition. In this embodiment the closed cutting configuration involves locating the tip of the tissue engagement device just proximal to an open distal end of the cutting sheath. Positioning a tissue engagement device (or stylet) in this manner reduces penetration of tissue into the inner hollow compartment 814 of the sheath 810. The transition to open configuration in this embodiment occurs when the tissue engagement device 220 is advanced relative to the distal open end of the sheath 810 to engage the ligamentum flavum.

Alternatively, the closed configuration may be provided using a conventional stylet to occlude an open-ended cutting sheath. The stylet remains within the cutting sheath during the advancement of the cutting sheath up to or slightly penetrating into the ligamentum flavum. The stylet is sized to fit within and occlude the hollow portion and open distal end of the cutting sheath. In one embodiment, the cutting sheath 810 is a needle with a hollow portion 814 and a sharp tip 816. In one aspect, this embodiment converts to an open configuration by removing the stylet once the ligamentum flavum is detected by the operator. After removal of the stylet, the hollow portion of the sheath is open and a tissue engagement device is allowed to pass through the sheath as shown and described above with regard to FIG. 14. Thereafter, the tissue engagement device is manipulated to engage the ligamentum flavum. Controlled advancement through the ligamentum flavum proceeds in a manner dependent upon the controlled advancement mode utilized by the particular tissue engagement device.

The cutting sheath and the tissue engagement device used in the apparatus for accessing the epidural space may be made from any of the materials typically used in medical devices including medical grade plastics, stainless steel, and other materials. Other exemplary materials include, but are not limited to, plastics and thermoplastics including acrylic, polyetheretherketone, polyvinylchloride, polycarbonate, polyethelene, polyetherimide, polytetrafluoroethylene, polysulfone, acrylonitrile-butadine-styrene or the like, or metals including, but not limited to, aluminum, steel, titanium, or a shape-memory alloy such as nitinol, or ceramics including, but not limited to, alumina, zirconia, carbides and the like. Additionally, the components of the inventive apparatus may include one or a combination of materials to endow a particular device with desired properties. The device surfaces may be further treated to endow them with desired properties such as smoothness or roughness, hydrophobicity or hydrophilicity, as well as other features. The sheath and tissue engagement device may be rigid or flexible or be comprised of both rigid and flexible portions. For example, the sheath distal penetrating end may be rigidly configured while the remaining shaft of the sheath is flexible. The components may be opaque, clear, radiopaque, radiolucent, echogenic, nonechogenic or contain combinations of such characteristics at different portions along its length. For example, the distal end of the tissue engagement device may be radiopaque while the main body is radiolucent.

In an embodiment with a flexible cable 295 connecting the tissue engagement device to a syringe and remote actuation mechanism, the flexible cable connection could be composed of plastic, rubber, metal, ceramic as listed above for the cutting sheath and tissue engagement device or any flexible and formable material or possibly a series of linkages of rigid pieces.

The tissue engagement device of the invention is preferentially fabricated from a rigid material designed to accommodate the required push, pull, and rotational forces applied during normal operation. Threaded engagement features and mechanisms may be machined or otherwise introduced such as via a molding process onto a tubular body to form the desired design and pattern.

The dimensions of the device are so configured to be comparable to devices currently used by those familiar with the art. The external diameter of the device can be configured to be in the range of 1-2 mm. The engagement components are situated along the region between the distal end of the tissue engagement device and nominally 6-10 mm behind the end to enable sufficient engagement of the ligamentum flavum through its thickness which is typically in the range of 2-4 mm. These dimensions serve to provide guidelines in the spirit of the invention and should not be construed as anything but.

The description of the above is meant to be illustrative of the scope and spirit of the invention. It will be obvious to one skilled in the art that many modifications can be made to the present invention without departing from the nature and scope thereof. The sizes and distances presented are for illustration purposes only and should not be construed to limit the scope of the invention.

What is claimed is:

1. An apparatus for accessing the epidural space in a mammal, comprising:
   a cutting sheath having an open proximal end and a distal end adapted to transition from a closed cutting configuration to an open configuration;
   a hollow portion within the sheath extending from the open proximal end along a longitudinal axis of the sheath;
   a tissue engagement device disposed within the hollow portion of the cutting sheath, the tissue engagement device having an elongate body with a proximal end and a blunt distal end;
   an engagement feature on a surface of the elongate body;
   an aperture formed in the distal end of the elongate body; and
   means for delivering fluid or an instrument out of the aperture, wherein the means for delivering is located within the elongate body in communication with the aperture and the elongate body proximal end.

2. The apparatus of claim 1 wherein the engagement feature on the surface of the elongate body is a screw thread.

3. The apparatus of claim 2 wherein the screw thread comprises an asymmetric thread form.

4. The apparatus of claim 2 wherein the screw thread comprises a reverse buttress thread form.

5. The apparatus of claim 1 wherein the engagement feature on the surface of the elongate body comprises a plurality of ridges.

6. The apparatus of claim 5 further comprising:
   a balloon positioned within the distal end of the tissue engagement device.

7. The apparatus according to claim 1 wherein the cutting sheath distal end transitions from a closed cutting configuration to an open configuration by moving the elongate body within the hollow portion of the cutting sheath.

8. The apparatus according to claim 7 wherein moving the elongate body within the hollow portion of the cutting sheath comprises sliding the elongate body within the hollow portion of the cutting sheath.

9. The apparatus according to claim 7 wherein moving the elongate body within the hollow portion of the cutting sheath comprises rotating the elongate body within the hollow portion of the cutting sheath.

10. The apparatus according to claim 1, the cutting sheath further comprising:
   at least one predefined movable section.

11. The apparatus according to claim 10, the cutting sheath further comprising:
   a hinge that joins the at least one predefined movable section to the distal end of the cutting sheath.

12. The apparatus according to claim 10 wherein the at least one predefined movable section is defined by a scoring pattern in a sidewall of the cutting sheath.

13. The apparatus according to claim 10 wherein the at least one predefined movable section is cut into the distal end of the sheath.

14. The apparatus according to claim 1 wherein the aperture is formed in the sidewall of the elongate body proximal to the blunt distal end.

15. The apparatus according to claim 1 wherein the aperture is formed in the blunt distal end.

16. An apparatus for accessing the epidural space in a mammal, comprising:
   a cutting sheath having an open proximal end and a distal end adapted to transition from a closed cutting configuration to an open configuration;
   a hollow portion within the sheath extending from the open proximal end to the distal end;
   a stylet placed within the hollow portion when the cutting sheath is in the closed cutting configuration;
   a tissue engagement device disposed within the hollow portion when the cutting sheath is in the open configuration, the tissue engagement device having an elongate body with a proximal end and a blunt distal end;
   an engagement feature on a surface of the elongate body;
   an aperture formed in the distal end of the elongate body; and
   means for delivering fluid or an instrument out of the aperture, wherein the means for delivering is located within the elongate body and is in communication with the aperture.

17. An apparatus for accessing the epidural space in a mammal, comprising:
   a cutting sheath having an open proximal end and a distal end adapted to transition from a closed cutting configuration to an open configuration;
   a hollow portion within the sheath extending from the open proximal end along a longitudinal axis of the sheath;
   a tissue engagement device disposed within the hollow portion of the cutting sheath, the tissue engagement device having an elongate body with a proximal end and a blunt distal end;
   an engagement feature on a surface of the elongate body;
   an aperture formed in the distal end of the elongate body; and
   means for delivering fluid or an instrument out of the aperture, wherein the means for delivering is located within the elongate body in communication with the aperture and the elongate body proximal end;
   wherein the engagement feature on the surface of the elongate body is configured to engage with a ligamentum flavum, and to translate relative to the ligamentum flavum in a controllable manner.

18. The apparatus of claim 1, wherein the aperture faces towards a direction that forms an angle with a longitudinal axis of the elongate body.

19. The apparatus of claim 1, wherein the instrument comprises a catheter.

20. The apparatus of claim 2, wherein the screw thread has a sharp cutting edge.

21. An apparatus for accessing the epidural space in a mammal, comprising:
   a cutting sheath having an open proximal end and a distal end adapted to transition from a closed cutting configuration to an open configuration;
   a hollow portion within the sheath extending from the open proximal end to the distal end;
   a stylet placed within the hollow portion when the cutting sheath is in the closed cutting configuration;
   a tissue engagement device disposed within the hollow portion when the cutting sheath is in the open configuration, the tissue engagement device having an elongate body with a proximal end and a blunt distal end;
   an engagement feature on a surface of the elongate body;
   an aperture formed in the distal end of the elongate body; and
   means for delivering fluid or an instrument out of the aperture, wherein the means for delivering is located within the elongate body and is in communication with the aperture;
   wherein the engagement feature on the surface of the elongate body is configured to engage with a ligamentum flavum, and to translate relative to the ligamentum flavum in a controllable manner.

22. The apparatus of claim 16, wherein the aperture faces towards a direction that forms an angle with a longitudinal axis of the elongate body.

23. The apparatus of claim 16, wherein the means for delivering comprises a conduit configured for delivering the fluid or the instrument out of the aperture, and wherein the aperture is unblocked for allowing the fluid or the instrument to be delivered therethrough.

24. The apparatus of claim 23, wherein the instrument comprises a catheter.

25. The apparatus of claim 16, wherein the engagement feature on the surface of the elongate body is a screw thread.

26. The apparatus of claim 25, wherein the screw thread has a sharp cutting edge.

27. The apparatus of claim 25, wherein the screw thread comprises an asymmetric thread form.

28. The apparatus of claim 25, wherein the screw thread comprises a reverse buttress thread form.

29. The apparatus of claim 16, wherein the engagement feature on the surface of the elongate body comprises a plurality of ridges.

* * * * *